United States Patent
Diederich

(10) Patent No.: US 7,427,159 B2
(45) Date of Patent: Sep. 23, 2008

(54) INTRAORAL DENTAL RADIOLOGY POSITIONING DEVICE FOR USE WITH X-RAY RECEPTOR

(76) Inventor: Jennifer A Diederich, 64 Smith Rd., Avon, CT (US) 06001

( * ) Notice: Subject to any disclaimer, the term of this patent is extended or adjusted under 35 U.S.C. 154(b) by 0 days.

(21) Appl. No.: 11/559,628

(22) Filed: Nov. 14, 2006

(65) Prior Publication Data
US 2008/0025467 A1    Jan. 31, 2008

Related U.S. Application Data

(63) Continuation-in-part of application No. 10/899,250, filed on Jul. 26, 2004, now Pat. No. 7,172,339.

(51) Int. Cl.
*A61B 6/14* (2006.01)
(52) U.S. Cl. .................. 378/168; 378/170
(58) Field of Classification Search .......... 378/145, 378/167, 168, 170, 204, 205
See application file for complete search history.

(56) References Cited

U.S. PATENT DOCUMENTS

| RE25,773 E | 5/1965 | Medwedeff et al. ......... 378/170 |
|---|---|---|
| 3,304,422 A * | 2/1967 | Medwedeff ................. 378/170 |
| 3,304,423 A | 2/1967 | Medwedeff ................. 378/170 |
| 3,745,344 A | 7/1973 | Updegrave ................. 378/170 |
| 4,507,798 A | 3/1985 | Welander ................... 378/170 |
| D281,353 S | 11/1985 | Sico, Jr. .................... D24/158 |
| 4,554,676 A | 11/1985 | Maldonado et al. ........ 378/170 |
| D283,157 S | 3/1986 | Maldonado et al. ........ D24/161 |
| 5,090,047 A | 2/1992 | Angotti et al. .............. 378/170 |
| 5,327,477 A | 7/1994 | Levy ......................... 378/168 |
| 5,416,822 A | 5/1995 | Kunik ....................... 378/162 |
| 6,343,875 B1 | 2/2002 | Eppinger et al. ........... 378/170 |
| 6,599,013 B1 | 7/2003 | Diederich .................. 378/170 |
| 7,056,015 B2 | 6/2006 | Diederich .................. 378/170 |
| 7,172,339 B2 | 2/2007 | Diederich .................. 378/168 |

OTHER PUBLICATIONS

Patterson Catalog. pp. 545, 546. (2001).
Goaz & White, Health Physics. Radiation Safety and Protection. pp. 53-68. (prior to 2000).

(Continued)

*Primary Examiner*—Courtney Thomas
(74) *Attorney, Agent, or Firm*—DeLio & Peterson, LLC; Peter W. Peterson

(57) ABSTRACT

A method for taking dental bitewing radiographs of a patient's teeth. A receptor positioning device is provided which includes a receptor holding member and an arm including a biting surface for engaging the patient's teeth. The device includes a collimation plate with a cross-shaped opening for passage of radiation from the x-ray machine. A pair of handles extends away from the plate for positioning the device, with one of the handles being radially aligned and the other of the handles being non-radially aligned. Each handle includes a polymeric grip incorporating an arm holder adjacent a base of the handle and having a rectangular opening for slidably receiving the arm and removably securing the collimation plate to the receptor holding member. One rectangular opening is radially aligned and the other rectangular opening is non-radially aligned. The method then includes aligning an x-ray machine with the collimation plate and passing radiation from the x-ray machine through the opening of the collimation plate to expose the receptor, while the patient's hand grasps the collimation plate handle.

20 Claims, 24 Drawing Sheets

OTHER PUBLICATIONS

Margraf Corp. Film Positioning Instruments. pp. 1-3. (http://www.margrafcorp.com/FPI.htm) (2002).

Margraf Corp. Rectangular Positioning Indicating Devices. pp. 1-2. (http://www.margrafcorp.com/RectPID.htm). (2002).

Practicon Dental Catalog. Fully Redesigned Rinn XCP Film Holders Improve Patient Comfort, Staff Efficiency. pp. 57 and 58. (prior to 2002).

Mackie X-ray Advertisment. RAPD Intra Oral System. (prior to 2002).

Dentsply Rinn Catalog. Film Holding Instruments. pp. 15, 16, 17 and 27. (1997).

Masel Cataog. Masel Precision X-Ray Film Holders. pp. 9-13. (1995).

\* cited by examiner

INTRAORAL DENTAL RADIOLOGY POSITIONING DEVICE FOR USE WITH X-RAY RECEPTOR

This application is a continuation-in-part of Ser. No. 10/899,250 filed Jul. 26, 2004.

BACKGROUND OF THE INVENTION

1. Field of the Invention

The present invention relates to devices for dental radiographic procedures or intraoral diagnostics, and more particularly, to intraoral dental radiology positioning devices relating to positioning x-ray film or receptors in a patient's mouth during radiographic procedures.

2. Description of Related Art

Intraoral x-ray diagnosis involves positioning an x-ray film within a patient's mouth next to the inner surface of the teeth or bone being studied. The film is then exposed to an x-ray beam generated outside the mouth and passing through the target. Known intraoral dental radiography typically employs a dental device having an alignment member including an x-ray film holding structure at one end, an aligning arm at another end, and a bite plate positioned between the ends. The alignment member (also known as an aiming ring) may include a collimation structure for collimation of an x-ray beam to conform more accurately to the size and shape of the x-ray film held by the film holding structure. A commonly prescribed dental radiograph is the "bitewing", whereby an image is acquired of the crowns of the teeth biting together and their surrounding socket bone. Also typical is film mounted in a holder that includes a bite block portion extending from the film in the direction of the external x-ray tube. The patient bites down on the bite block with the target teeth and holds the film in position next to the target.

Many dental radiographic techniques utilize beams of circular cross-section despite the fact that the dental films are typically rectangular in shape. A disadvantage of known devices is that the cross-sectional area of the beam used by the radiographic technique is typically larger than the surface area of the x-ray film. When the cross-sectional area of the beam does not match the film size, the patient can be exposed to unnecessary radiation that irradiates tissues beyond the borders of the dental film. Typical film positioning instruments may also allow unwanted x-radiation to pass through the film holding instrument.

Another disadvantage of current x-ray film positioning instruments is that there can be errors in aiming the x-ray. These errors are frequently associated with a rectangular position-indicating device attached to an x-ray machine. Also, there can be errors in orientation of the long axis of the substantially rectangular typical position indicating devices with the long axis of the film in the patient's mouth. Aiming and orientation errors expose the patient to needless retakes of radiographs. Moreover, if a rectangular positioning device is used, it must be specifically oriented for vertical or horizontal receptor orientation, and must be re-positioned if the receptor orientation is changed.

A further disadvantage of current x-ray film positioning instruments is that the patient can only bite on the bite plate to assist in positioning and holding a film positioning device in the mouth. Typical devices may be difficult to grasp and manipulate in the patient's mouth making it problematic for the patient to assist in positioning the instrument, particularly during the x-ray exposure itself.

SUMMARY OF THE INVENTION

Bearing in mind the problems and deficiencies of the prior art, it is therefore an object of the present invention to provide a device which will reduce patient exposure of x-radiation, and which will reduce aiming error and cone cuts.

It is yet another object of the present invention to provide a device which will universally adapt to traditional film and electronic/digital receptors, and also to typical film holding instrument aiming rings.

It is another object of the present invention to provide a device that minimizes movement of the device in the patient's mouth, and maximizes sharpness of the acquired image on the film.

It is yet another object of the present invention to provide a device which precisely sets the x-ray source to align with the receptor.

It is yet another object of the present invention to provide a device which minimizes patient discomfort and malpositioning.

It is another object of the present invention to provide a device that can rotate the orientation of the central rectangular opening of a collimator.

Still other objects and advantages of the invention will in part be obvious and will in part be apparent from the specification.

The above and other objects, which will be apparent to those skilled in the art, are achieved in the present invention which is directed to a receptor positioning device for taking dental bitewing radiographs of a patient's teeth comprising a receptor holding member adapted to receive a receptor for exposing x-radiation from the x-ray machine and an arm secured to the receptor holding member and including a biting surface for engaging the patient's teeth to secure the device in the patient's mouth. The device further includes a collimation plate having a substantially flat surface for aligning with an x-ray machine and made of a material and sized sufficient to attenuate undesired radiation from the patient's mouth. An opening in the plate surface is provided for passage of radiation from the x-ray machine, with the opening at least partially corresponding in shape to a receptor in the receptor holding member. A handle extends away from the plate for positioning the device. The collimation plate includes a reinforced arm holder adjacent a base of the handle and having an opening therein for slidably receiving the arm and removably securing the collimation plate to the receptor holding member.

The collimation plate may be made of a metal or a high gravity compound, and further includes polymeric grips on the handles incorporating the arm holder, with the collimation plate having a cut-out portion adjacent a base of the handle through which the arm-receiving opening of the polymeric arm holder extends. The device may include a pair of handles, each handle having a polymeric portion with an arm-receiving opening, wherein one of the handles is radially aligned with the collimation plate opening and the other of the handles is non-radially aligned with the collimation plate opening.

Preferably, the arm-receiving opening of the arm holder is rectangular and the collimation plate has a cut-out portion adjacent a base of the handle on at least two sides of the rectangular arm-receiving opening. Where the device includes a pair of handles, each handle has an arm holder with an arm-receiving rectangular opening, with one of the arm-receiving rectangular openings being radially aligned with the collimation plate opening and the other of the arm-receiving rectangular openings being non-radially aligned with the collimation plate opening.

The collimation shield opening is preferably a cross-shaped intersection of two non-square rectangles having members with a length and a width, the length of the cross members being equal to a longer side length of the rectangles and the width of the cross-members being equal to a shorter side length of the rectangles.

In another aspect, the present invention is directed to a receptor positioning device for taking dental bitewing radiographs of a patient's teeth comprising a receptor holding member adapted to receive a receptor for exposing x-radiation from the x-ray machine and an arm secured to the receptor holding member and including a biting surface for engaging the patient's teeth to secure the device in the patient's mouth. The device further includes a collimation plate having a substantially flat surface for aligning with an x-ray machine and made of a material and sized sufficient to attenuate undesired radiation from the patient's mouth. An opening in the plate surface for passage of radiation from the x-ray machine is cross-shaped and corresponding in shape to an outline of two intersecting non-square rectangles to permit passage of x-rays to a receptor in the either a vertical or horizontal position in the receptor holding member. The device includes a handle extending away from the plate for positioning the device. The collimation plate is securable to the arm securing the receptor holding member.

The collimation plate may be made of a metal or a high gravity compound and further includes polymeric grips on the handles incorporating an arm holder adjacent a base of the handle and having an opening therein for slidably receiving the arm and removably securing the collimation plate to the receptor holding member.

Preferably, the arm-receiving opening of the arm holder is rectangular and the collimation plate has a cut-out portion adjacent a base of the handle on at least two sides of the rectangular arm-receiving opening. More preferably, the device includes a pair of handles, with each handle having an arm holder with an arm-receiving rectangular opening. One of the arm-receiving rectangular openings is radially aligned with the collimation plate opening and the other of the arm-receiving rectangular openings is non-radially aligned with the collimation plate opening. Each handle may have a polymeric portion with an arm-receiving rectangular opening, with one of the handles being radially aligned with the collimation plate opening and the other of the handles being non-radially aligned with the collimation plate opening.

In a further aspect, the present invention is directed to a receptor positioning device for taking dental bitewing radiographs of a patient's teeth comprising a receptor holding member adapted to receive a receptor for exposing x-radiation from the x-ray machine and an arm secured to the receptor holding member and including a biting surface for engaging the patient's teeth to secure the device in the patient's mouth. The device further includes a collimation plate having a substantially flat surface for aligning with an x-ray machine and made of a material and sized sufficient to attenuate undesired radiation from the patient's mouth, with an opening in the plate surface for passage of radiation from the x-ray machine. A pair of handles extends away from the plate for positioning the device, with one of the handles being radially aligned with the collimation plate opening and the other of the handles being non-radially aligned with the collimation plate opening. The collimation plate is securable to the arm securing the receptor holding member.

The collimation plate may be made of a metal or a high gravity compound, and further includes polymeric grips on the handles incorporating an arm holder adjacent a base of the handle and having an opening therein for slidably receiving the arm and removably securing the collimation plate to the receptor holding member. Preferably, the arm-receiving opening of the arm holder is rectangular and the collimation plate has a cut-out portion adjacent a base of the handle on at least two sides of the rectangular arm-receiving opening. One arm-receiving rectangular opening may be radially aligned with the collimation plate opening and another aim-receiving rectangular opening may be non-radially aligned with the collimation plate opening.

The opening may be a cross-shaped intersection of two non-square rectangles having members with a length and a width, the length of the cross members being equal to a longer side length of the rectangles and the width of the cross-members being equal to a shorter side length of the rectangles.

In a related aspect, the present invention provides a method for taking dental bitewing radiographs of a patient's teeth comprising providing a receptor positioning device including a receptor holding member adapted to receive a receptor for exposing x-radiation from the x-ray machine, and an arm secured to the receptor holding member and including a biting surface for engaging the patient's teeth to secure the device in the patient's mouth. The device includes a collimation plate having a substantially flat surface for aligning with an x-ray machine and made of a material and sized sufficient to attenuate undesired radiation from the patient's mouth, with an opening in the plate surface for passage of radiation from the x-ray machine. A pair of handles extends away from the plate for positioning the device, with one of the handles being radially aligned with the collimation plate opening and the other of the handles being non-radially aligned with the collimation plate opening. The collimation plate is secured to the arm securing the receptor holding member. The method then includes providing a receptor on the receptor holding member, positioning the receptor holding member in the patient's mouth and the patient's teeth on the biting surface, and adjusting the position of the receptor positioning device by the patient grasping a handle extending away from the collimation plate. The method further includes aligning an x-ray machine with the substantially flat surface of the collimation plate and passing radiation from the x-ray machine through the opening of the collimation plate to expose the receptor, while the patient's hand grasps the collimation plate handle.

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DESCRIPTION OF THE PREFERRED EMBODIMENT(S)

Figure 1:
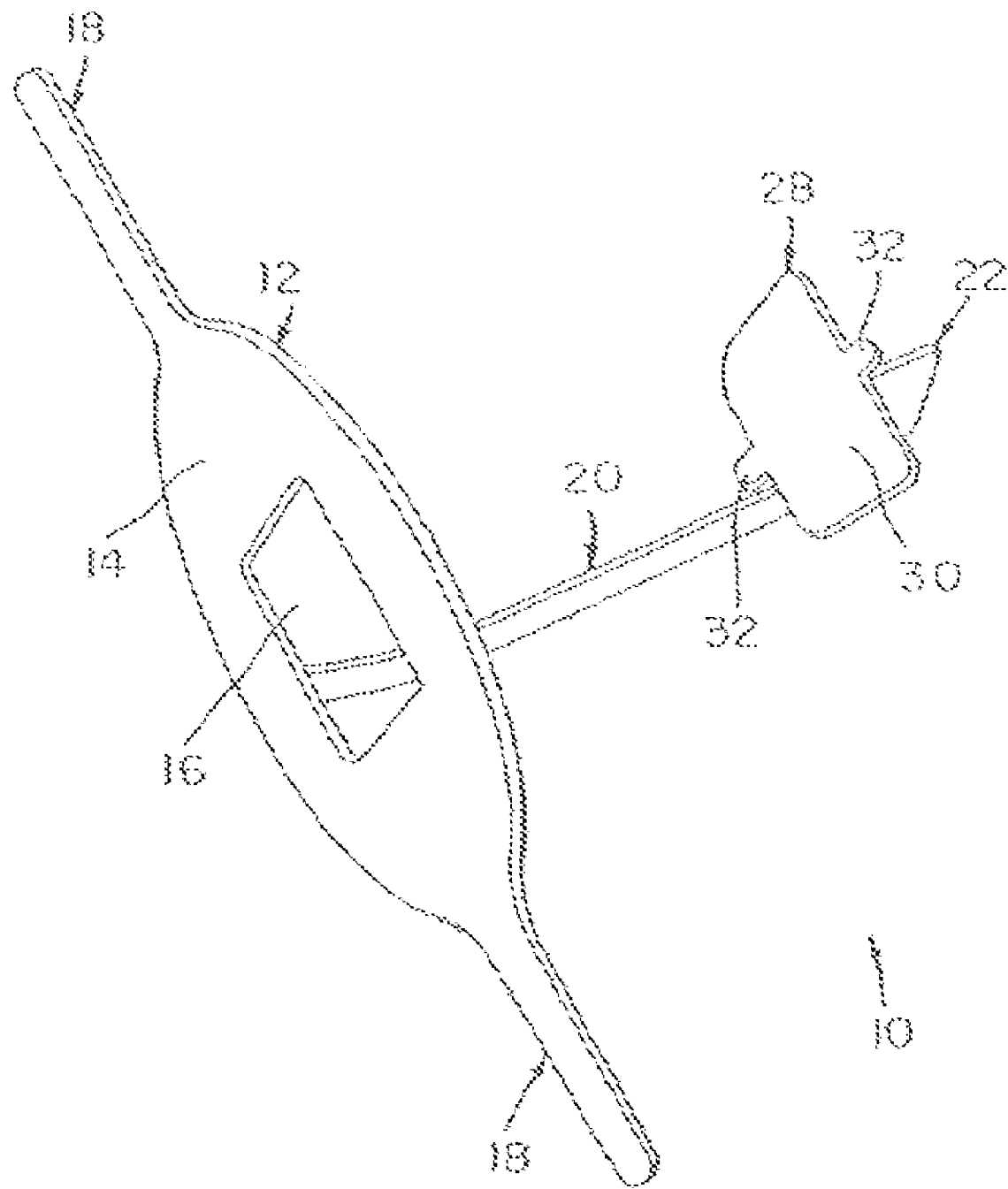
FIG. 1 is a perspective view of one embodiment of the receptor positioning device of the present invention.

In describing the preferred embodiment of the present invention, reference will be made herein to FIGS. 1-33 of the drawings in which like numerals refer to like features of the invention.

A preferred embodiment 10, shown in FIGS. 1-6 and 11, depicts one embodiment of the intraoral dental radiology receptor positioning device of the present invention. Referring to FIGS. 1-4, the receptor positioning device includes a substantially flat collimation plate 12, having a surface area 14. The surface area 14 defines a substantially central rectangular opening 16. The collimation plate 12 further includes opposing elongated handles 18 extending outward on opposite sides thereof. The receptor positioning instrument 10 further includes an elongated arm 20 and a film or electronic receptor holding member 28 having a back plate 30 and clips 32 for holding x ray film or electronic receptors. The elongated arm 20 is connected at a bent first end 40 to the back of the collimation plate 50, preferably, by welding or other rigid connection. The elongated arm further includes a second end 22 attached to the rear surface 52 of the back plate 30 of the receptor holding member 28, opposite collimator plate 12.

Figure 3:
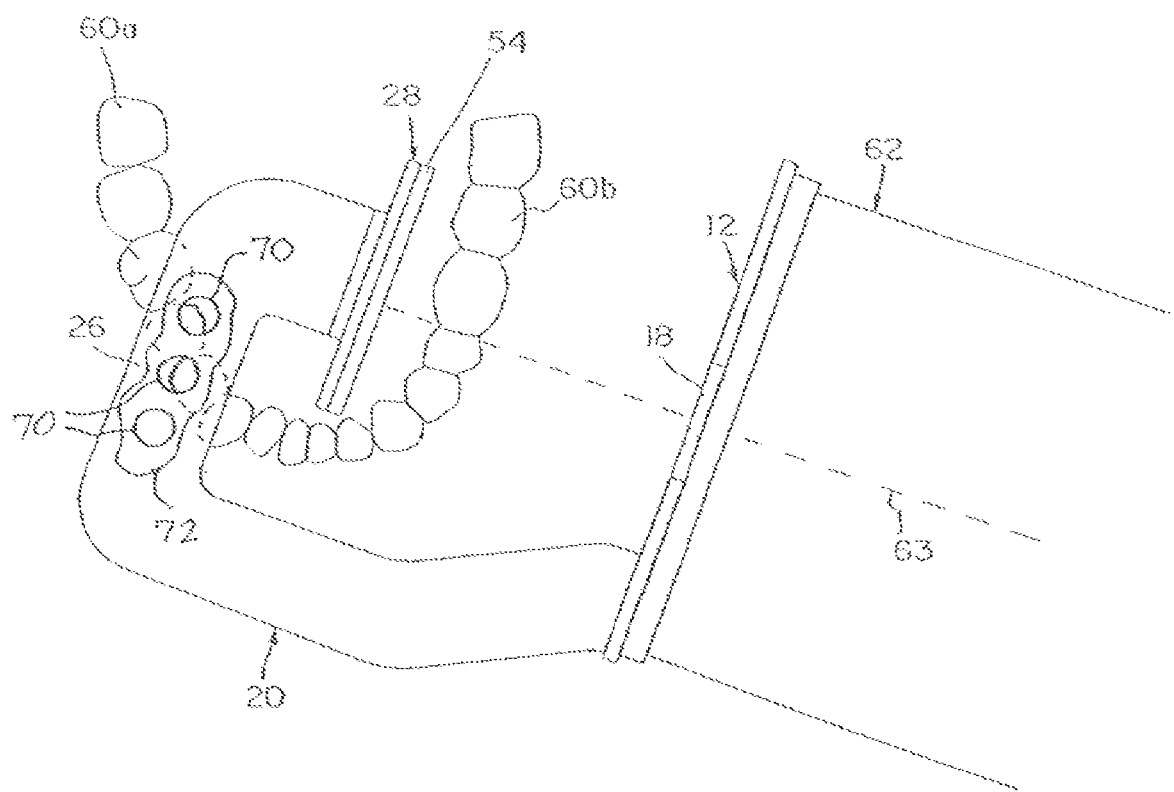
FIG. 3 is a side elevational view of the receptor positioning device shown in FIG. 1 depicting the position of the patient's teeth.
Figure 4:
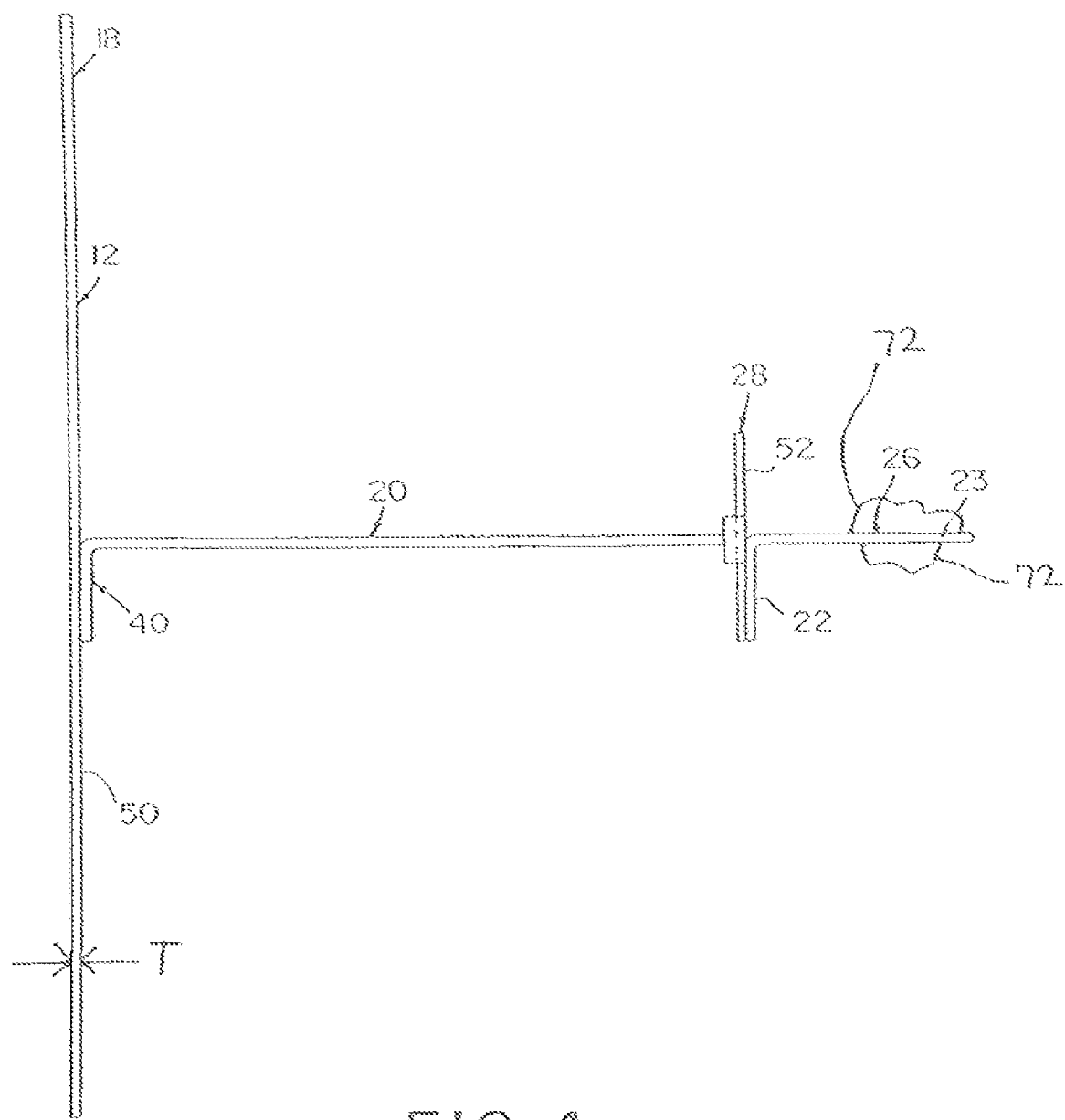
FIG. 4 is another side view of the receptor positioning device shown in FIG. 1 rotated 180° from the view in FIG. 3.
Figure 11:
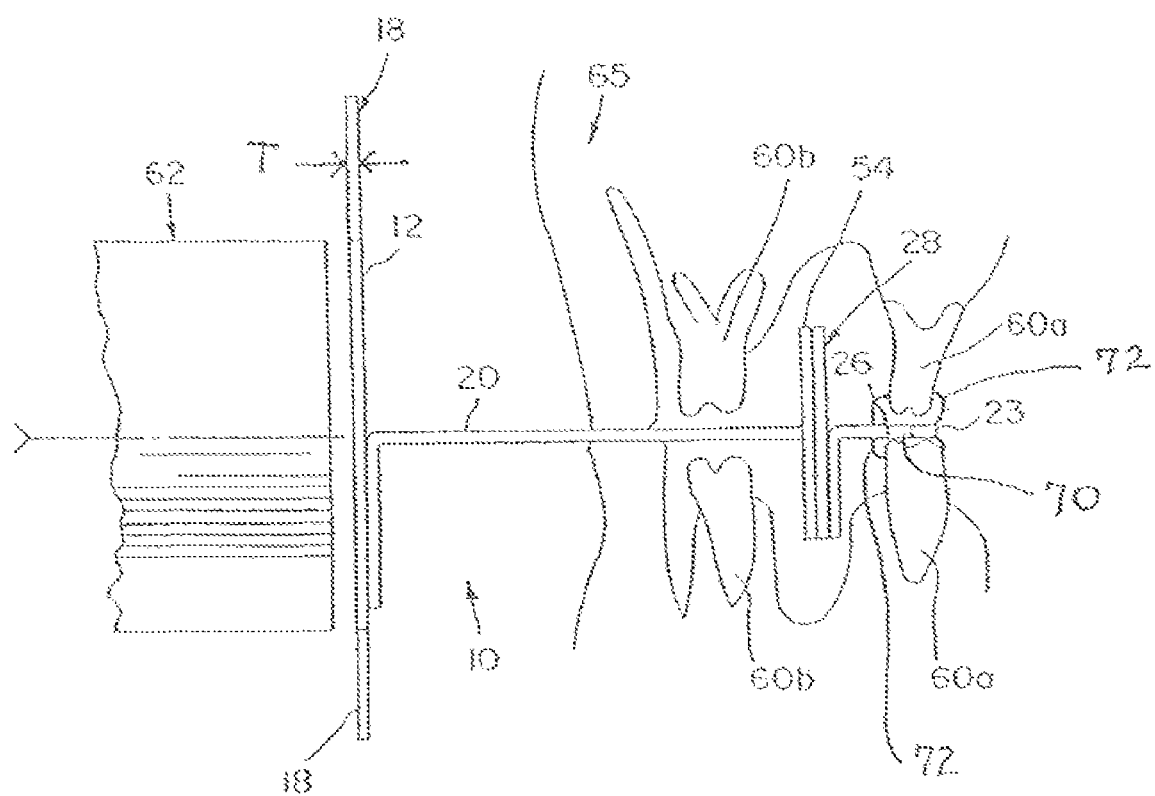
FIG. 11 is a side view of the receptor positioning device shown in FIG. 1 depicting the patient's teeth biting the device and the x-ray machine in position.

The film or electronic receptor holding member 28 back plate 30 is preferably of metal and the opposing clips 32 are designed and adapted to receive and grasp a removable film or digital-electronic receptor 54. The elongated arm 20 includes a flat upper surface 26 adapted to receive a patient's teeth. The patient's teeth 60a on one side of the mouth are positioned to grip the substantially flat biting surface 26 of the elongated arm 20, as shown in FIG. 3. The biting surface receiving portion is normally incompressible. Optionally, biting surface 26 on arm 20, behind the receptor plate 54, includes a plurality of circular perforations or openings, for example the three 6 mm diameter openings 70 longitudinally spaced 8 mm apart as shown in FIG. 3. These openings accommodate a curable elastomeric impression material 72, on either side of biting surface 26 (see also FIGS. 4-6, which may be used to create and register with the unique occlusion pattern of the patient's teeth, as also shown in FIG. 11. This registration may be removed, archived and reused to create reproducible x-ray images of the teeth in repeated sequential exposures over time.

The film or receptor 54 held on the back plate 30 by the clips 32 of the receptor holding member 28 is positioned behind the desired teeth 60b to be exposed, on the opposite side of the patient's mouth. Preferably, the back plate 30 and receptor 54 are parallel to collimation plate 12. The film or receptor 54 is thereby positioned to be exposed to an x-ray from the x-ray machine 62 to show the condition of teeth 60b, as shown further in FIG. 11.

Figure 2:
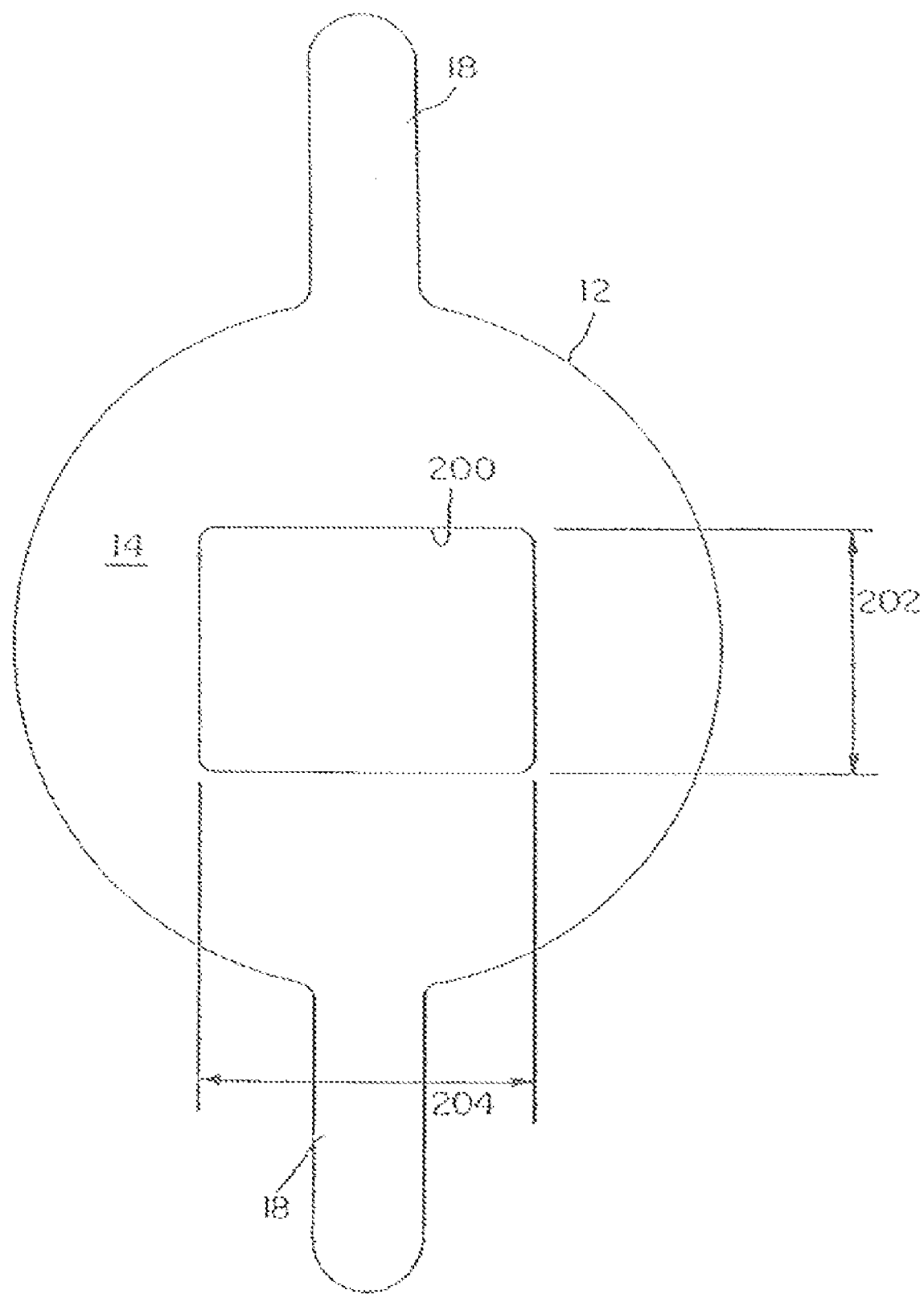
FIG. 2 is a front elevational view of the collimation plate of the device shown in FIG. 1.

Referring to FIG. 2, the collimation plate 12 further includes a preferably rectangular opening 200 positioned substantially in the center of the collimation plate 12. The opening 16 has a vertical dimension 202, and a horizontal dimension 204. In the preferred embodiment shown in FIGS. 1 and 2, the vertical dimension 202 of the opening is about 1.210 in. (3.1 cm), and the horizontal dimension 204 is preferably about 1.552 in. (3.9 cm). The collimation plate 12 is adapted to axially align the x-ray machine's position indicating cylinder device 62 with the receptor 54, as shown by the x-ray centerline 63. It does this in two ways. First, the x-ray machine is easily centered because the two devices, 12, 62, have substantially the same diameter. Axial offset would be apparent by extension of the outer edge of collimation plate 12 beyond the outer rim of the x-ray machine position indicating cylinder device 62. Second, substantially full, flat contact of the collimation plate 12 with the x-ray machine's position indicating cylinder device 62, as shown in FIG. 3, would assure optimal alignment of the x-ray receptor with the x-ray beam.

The orientation and size of the rectangular collimation opening described above is for use with the adult size horizontal bitewing radiographic examination of patients with normal anatomy and dentitions. Other sizes may be made for small children or for other uses. While existing commercially available metal collimation plates generally have on the order of 0.050 in. (1.27 mm) thickness, the inventor's dosimetry studies have shown that this thickness still permits a substantial amount of radiation to penetrate and expose the patient to needless additional radiation. Preferably, the thickness T of the collimation plate (FIG. 4) has at least 0.075 in. (1.9 mm) thickness, more preferably 0.080 (2.0 mm) or 0.100 in. (2.5 mm) or more to block such excess radiation.

Figure 5:
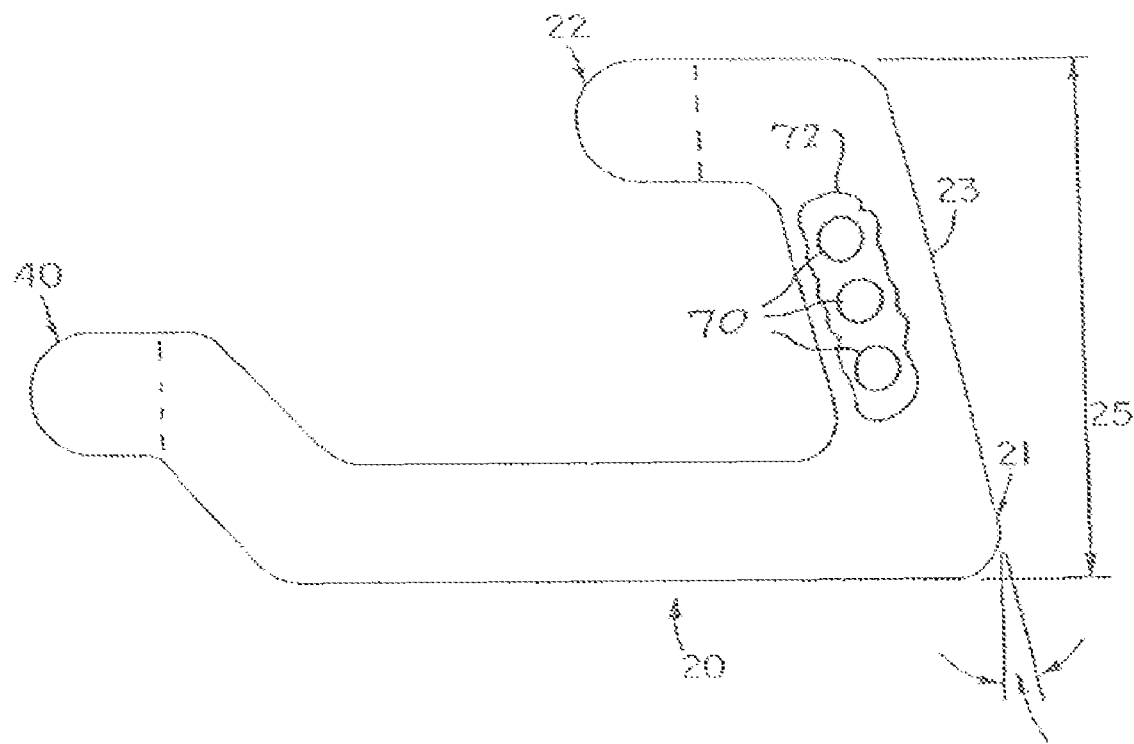
FIG. 5 is a side elevational view of the elongated arm of the receptor positioning device shown in FIG. 1.
Figure 6:
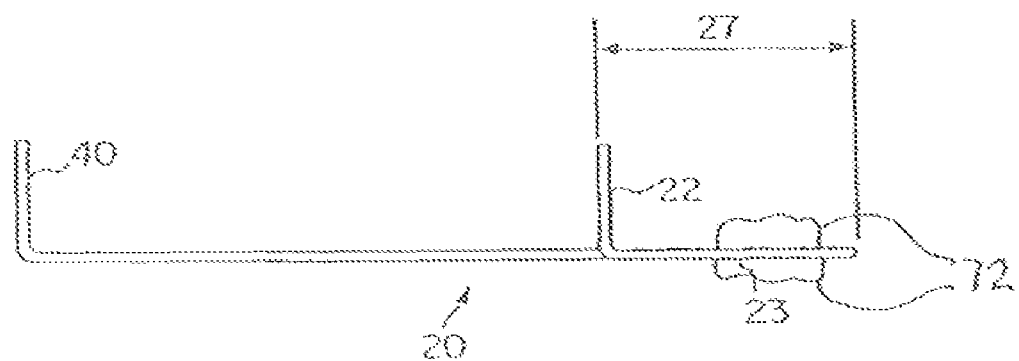
FIG. 6 is a side view of the elongated arm of FIG. 5.

Referring to FIGS. 5 and 6, the substantially flat elongated arm 20 of the preferred embodiment shown in FIG. 1 is shown including the first end 40, the second end 22 a short member 23 (on which biting surface 26 is located) having a first length 25, and an angled portion 21. FIG. 5 shows arm 20 as a flat blank prior to forming at the dotted lines, while FIG. 6 shows arm 20 after forming, where both ends 22 and 40 are bent approximately 90°. The second end 22 of the elongated arm 20, and the outer edge of the angled portion 21 define a first dimension 27. The first dimension 27 is preferably about 1.25 in. (3.2 cm), and the first length 25 is preferably about 2.54 in. (6.45 cm). The outer edge of the short member 23 and the vertical plane define an angle 29 which determines the angulation of the short member 23 of the elongated arm 20. The preferred angle 29 is about 12°. These dimensions and angles are preferred for three reasons. First, the dimension of the elongated arm is consistent with optimal placement of an x-ray receptor in mouths with normal anatomy and dentitions ranging in size from that of a child (8 years and up) to very large. Second, the dimension of the elongated arm is compatible with accommodating conventional film and digital-electronic receptors currently available. Third, the dimension of the elongated arm is compatible with accommodating the x-rays machine's position indicating cylinder device in optimal configuration with the receptor in the patient's mouth.

Figure 7:
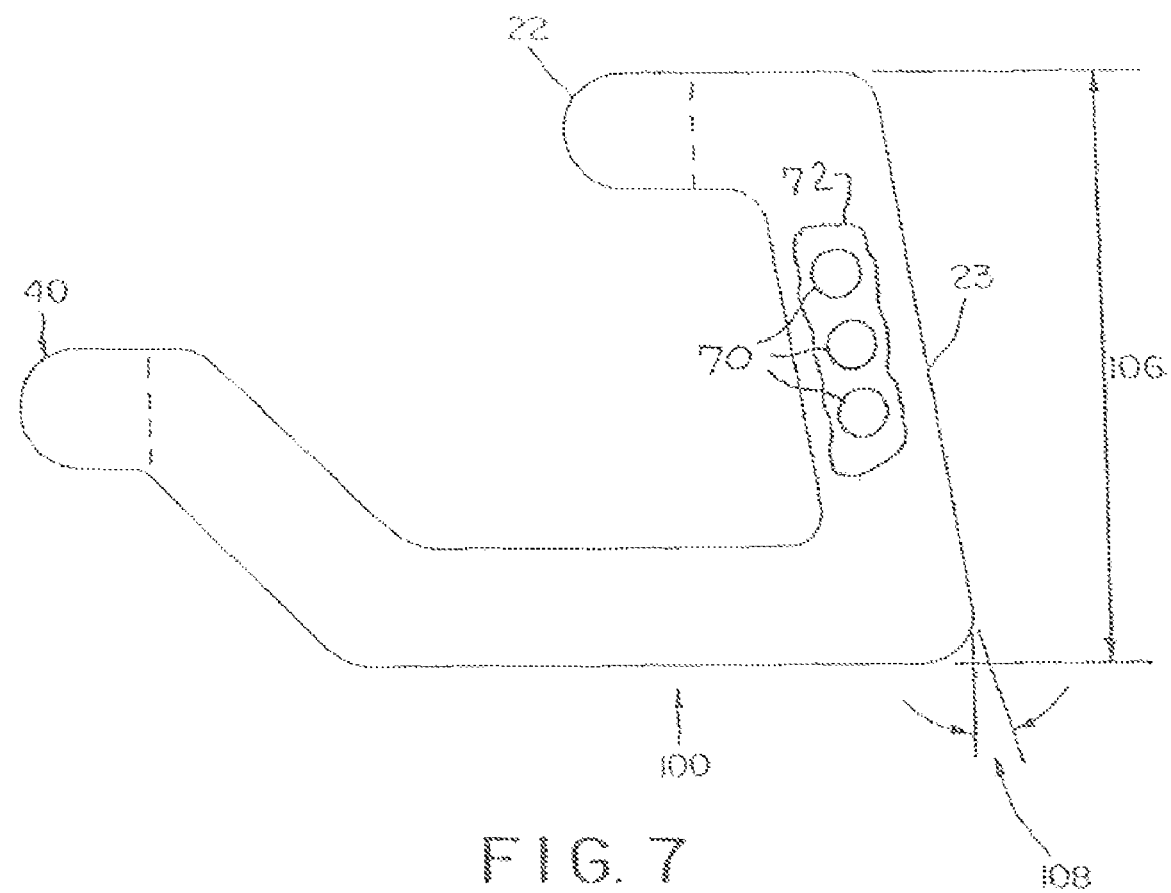
FIG. 7 is a side elevational view of another embodiment of an elongated arm of the receptor positioning device shown in FIG. 1.
Figure 8:
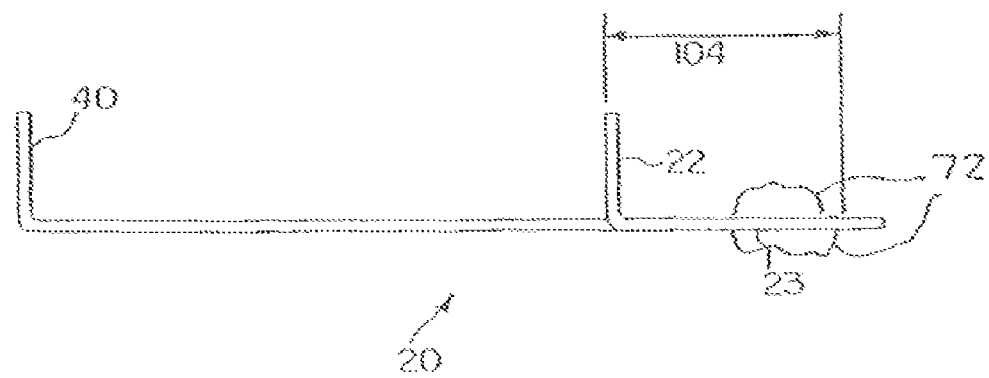
FIG. 8 is a side view of the elongated arm of FIG. 7.

Referring to FIGS. 7 and 8, another embodiment of an elongated arm 100 is shown which can be used with the receptor positioning device 10 shown in FIGS. 1-4. The elongated arm 100 includes the first end 40, the second end 22, the angled portion 21, and the short member 23 as in the embodiment shown in FIGS. 5 and 6. Again, FIG. 7 shows arm 20 as a flat blank prior to forming at the dotted lines, while FIG. 8 shows arm 20 after forming, where both ends 22 and 40 are bent approximately 90°. However, here the short member has a second length 106 which is more than the dimension 25 of the embodiment shown in FIGS. 1 and 5-6. The second length 106 is preferably about 2.85 in. (7.2 cm). The second end 22 of the elongated arm 20, and the outer edge of the angled portion 21 define a second dimension 104 which is less than the first dimension 27 of the embodiment shown in FIGS. 1 and 5-6. The second dimension 104 is less than the first dimension shown in FIG. 5 and preferably about 1.10 in. (2.8 cm). The outer edge of the short member 23 and the vertical plane define an angle 108 which is less than or more acute than the angle 29 of the embodiment shown in FIGS. 5 and 6 and is preferably about 7°. The more acute angle 108 better accommodates deep overbite occlusions. This other embodiment of the elongated arm has a dimension that is easily accommodated in mouths that have anatomy with deep overbites (retrognathic mandibles) ranging in size from that of a child to a large adult.

Figure 9:
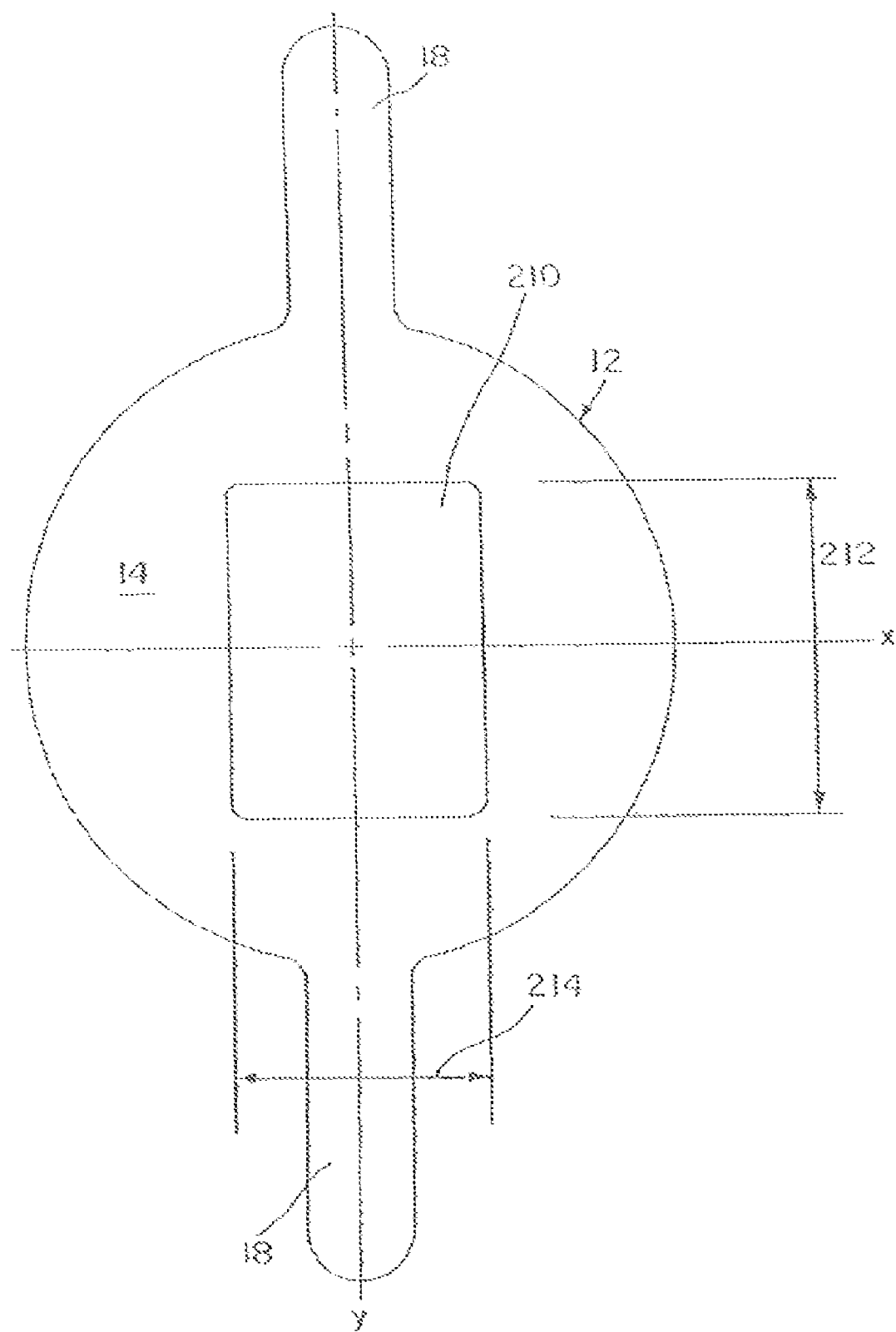
FIG. 9 is a front elevational view of another collimation plate for use with the receptor positioning device shown in FIG. 1 having a rectangular hole of different dimensions.
Figure 10:
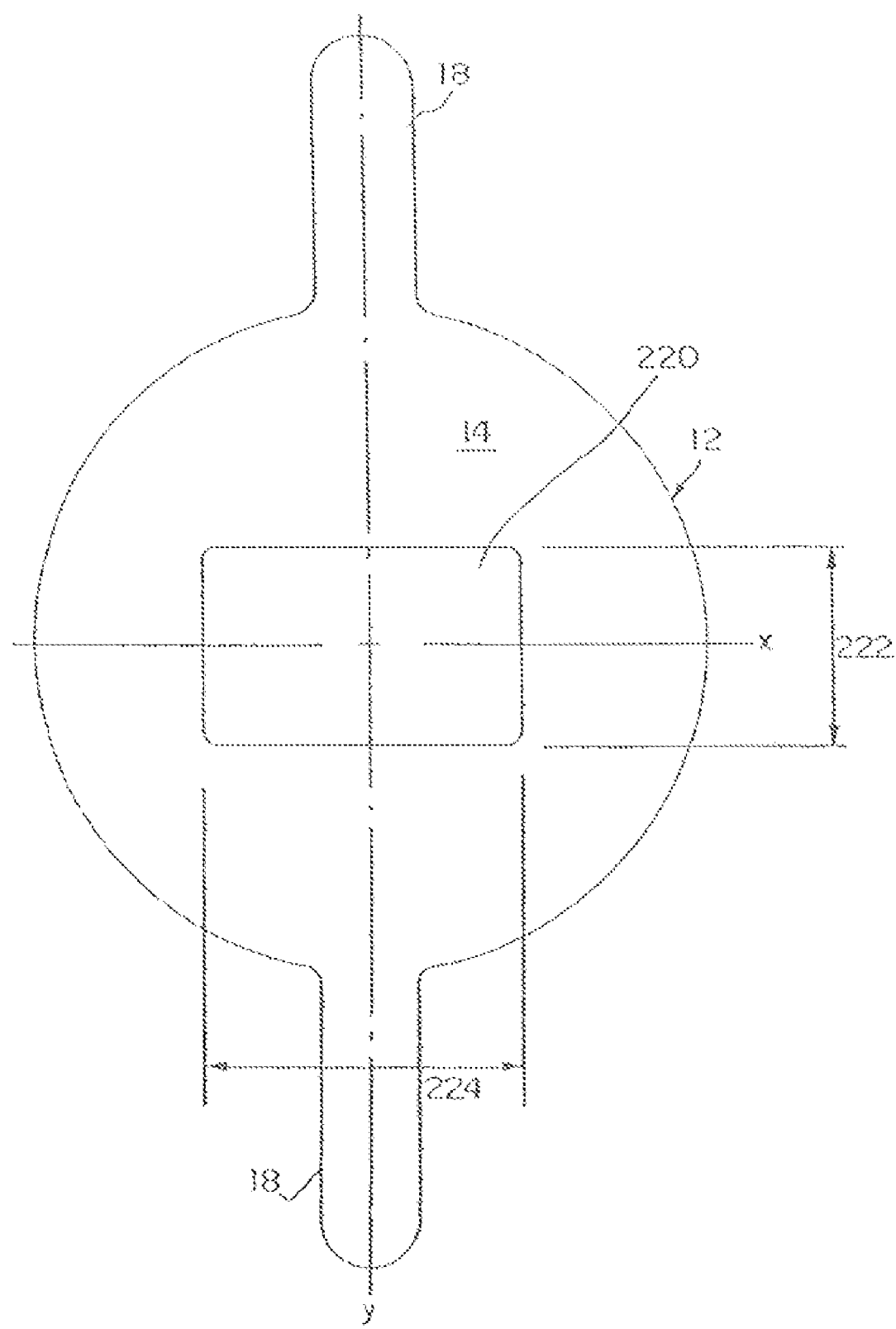
FIG. 10 is a front elevational view of another collimation plate for use with the receptor positioning device shown in FIG. 1 having a rectangular hole of still different dimensions.

Referring to FIGS. 9-10, other embodiments of a collimation plate 12 are shown including opposing elongated handles 18. Referring to FIG. 9, the collimation plate 12 further includes a preferably rectangular opening 210 positioned substantially in the center of the collimation plate 12, where the length of the opening 210 is smaller than the width. The opening 210 has a vertical dimension 212, and a horizontal dimension 214. In this embodiment, the vertical dimension 212 of the opening is preferably about 1.552 in. (3.9 cm), and the horizontal dimension 214 is preferably about 1.210 in. (3.1 cm). This embodiment offers a different positioning of the opening to correspond to an adult receptor or film held in the receptor holding member 28. The orientation and size of the rectangular collimation opening is for use with the adult size vertical bitewing radiographic examination. This is useful for observing compromised dentitions (with large restorations and height of alveolar crest bone decreased by marginal periodontal disease) that would not be visualized on horizontal bitewing images.

Referring to FIG. 10, the collimation plate 12 further includes a preferably rectangular opening 220 positioned substantially in the center of the collimation plate 12. The opening 220 has a vertical dimension 222, and a horizontal dimension 224. In this embodiment the vertical dimension 222 of the opening is about 1.000 in. (2.5 cm), and the horizontal dimension 224 is preferably about 1.552 in. (3.9 cm). This embodiment is designed to correspond to a child's receptor or film held in the receptor holding member 28. The size and orientation of the rectangular collimation opening is for use for horizontal bitewing examinations in small children (4-8 years) and very small adults or adults with limited ability to open their mouths.

Figure 12:
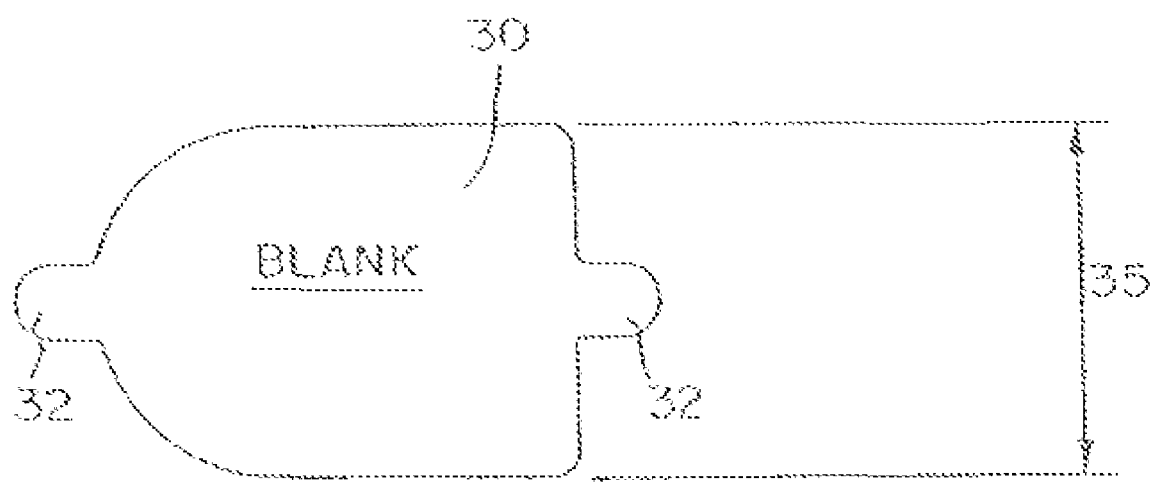
FIG. 12 is a back plate for receiving receptor of the receptor positioning device shown in FIG. 1.
Figure 13:
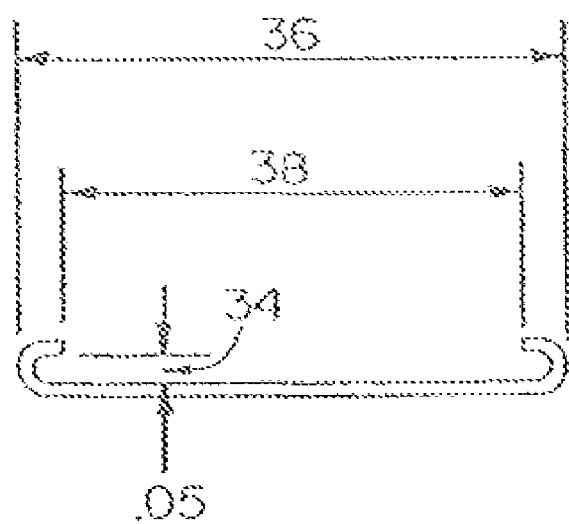
FIG. 13 is a side elevational view of the back plate of FIG. 12.

Referring to FIGS. 12 and 13, the back plate 30 is shown of the device of FIG. 1. FIG. 12 shows the flat blank for plate 30 and FIG. 13 shows plate 30 after forming. The back plate 30 includes the clips 32 and preferably has an overall length 36 of about 1.71 in. (4.3 cm), and a dimension between the clips 38 of preferably about 1.578 in. (4.0 cm), as they are shown formed and curled in FIG. 13. The preferred dimension 34 between the back plate 30 and the formed clip 32 is about 0.05 in. (1.3 mm). The overall length 36 of the back plate 30 with the clips 32 curled, as shown in FIG. 13, is preferably about 1.71 in. (4.3 cm), and the length 38 between the curled clips 32 is preferably about 1.578 in. (4.0 cm). The width 35 of the back plate 30 is preferably about 1.20 in. (3.05 cm). The dimensions herein accommodate standard intraoral dental film.

Figure 14:
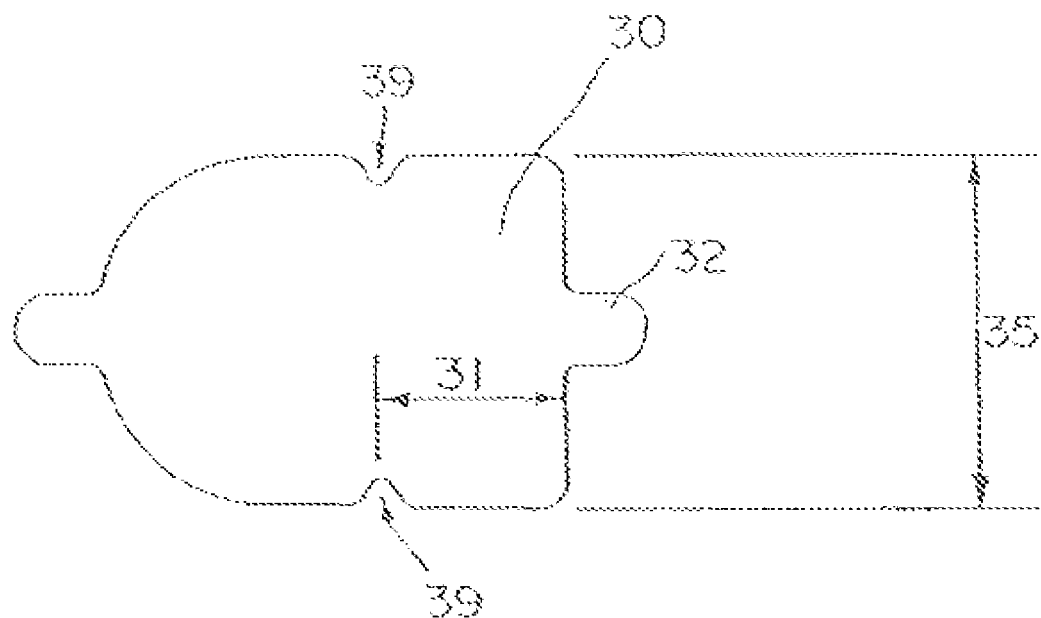
FIG. 14 is another embodiment of a back plate for receiving electronic receptors of the receptor positioning device shown in FIG. 1, having opposing notches.
Figure 15:
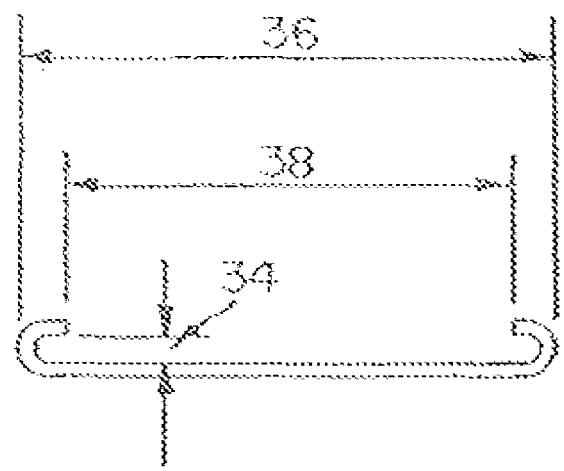
FIG. 15 is a side elevational view of the back plate of FIG. 14.
Figure 16:
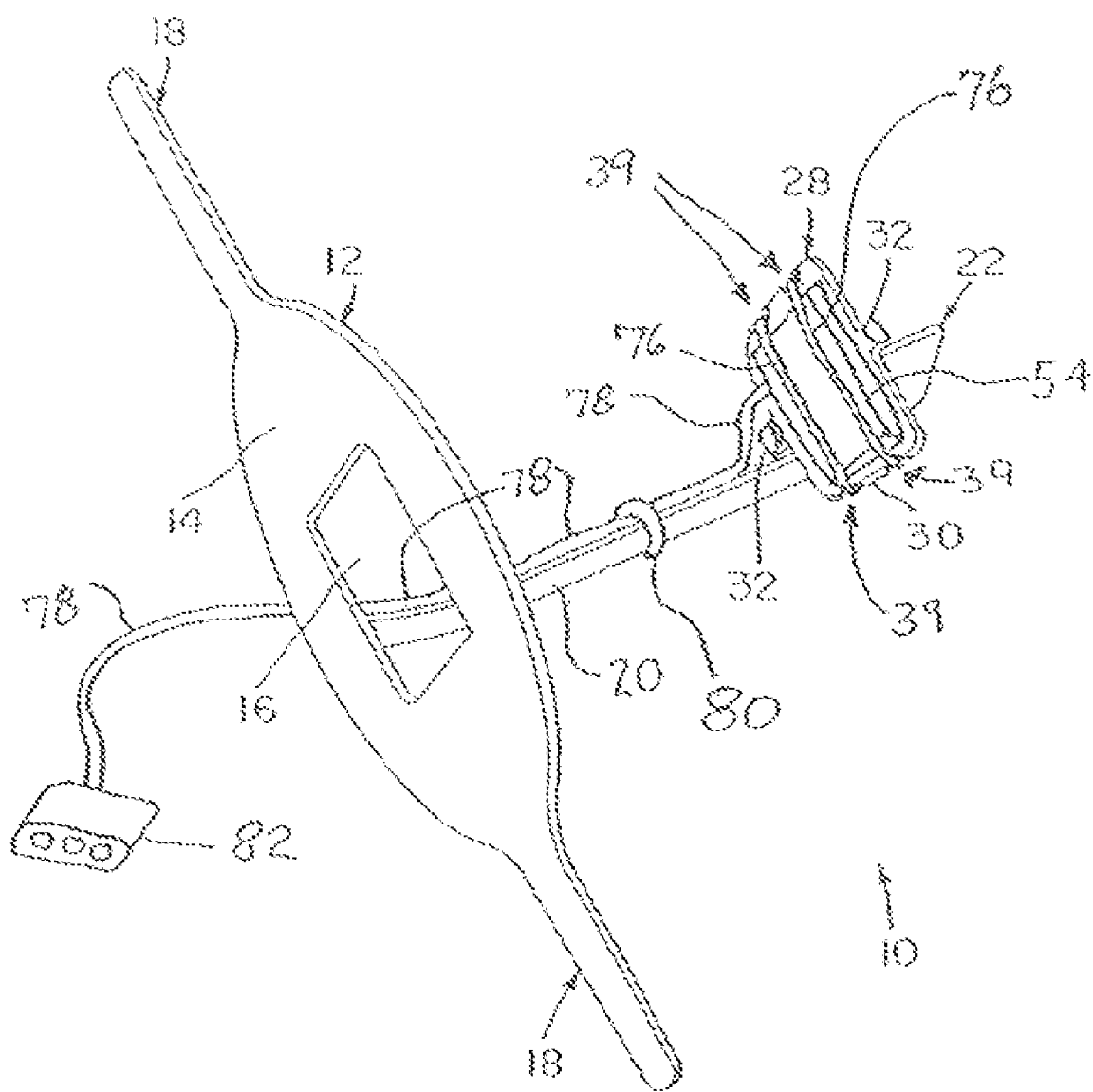
FIG. 16 is a perspective view of the receptor positioning device of the present invention incorporating a digital receptor.
Figure 17:
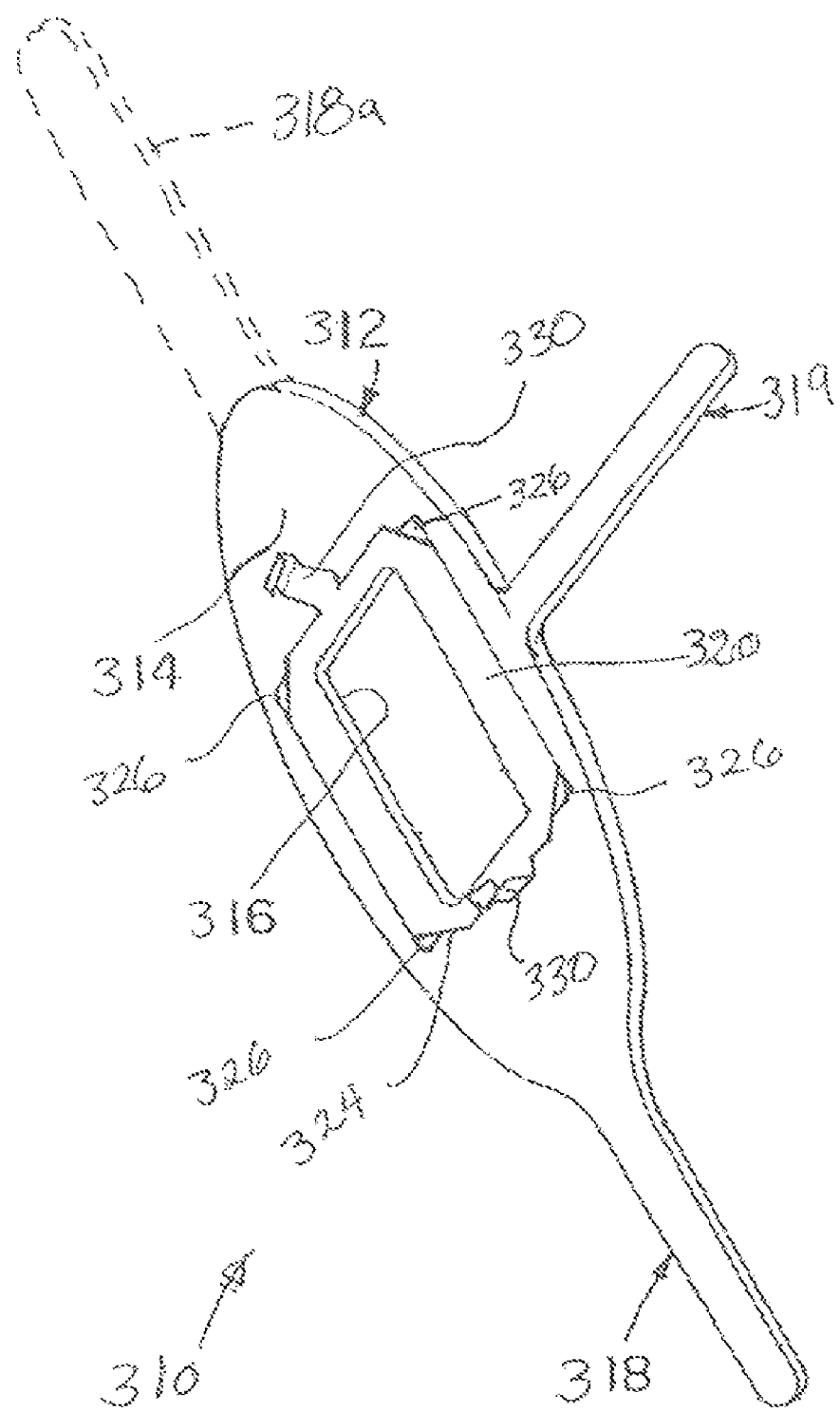
FIG. 17 is a perspective view of an embodiment of the collimation/shield device of the present invention, with attachment member, intended for use with a typical prior art film holding instrument.
Figure 18:
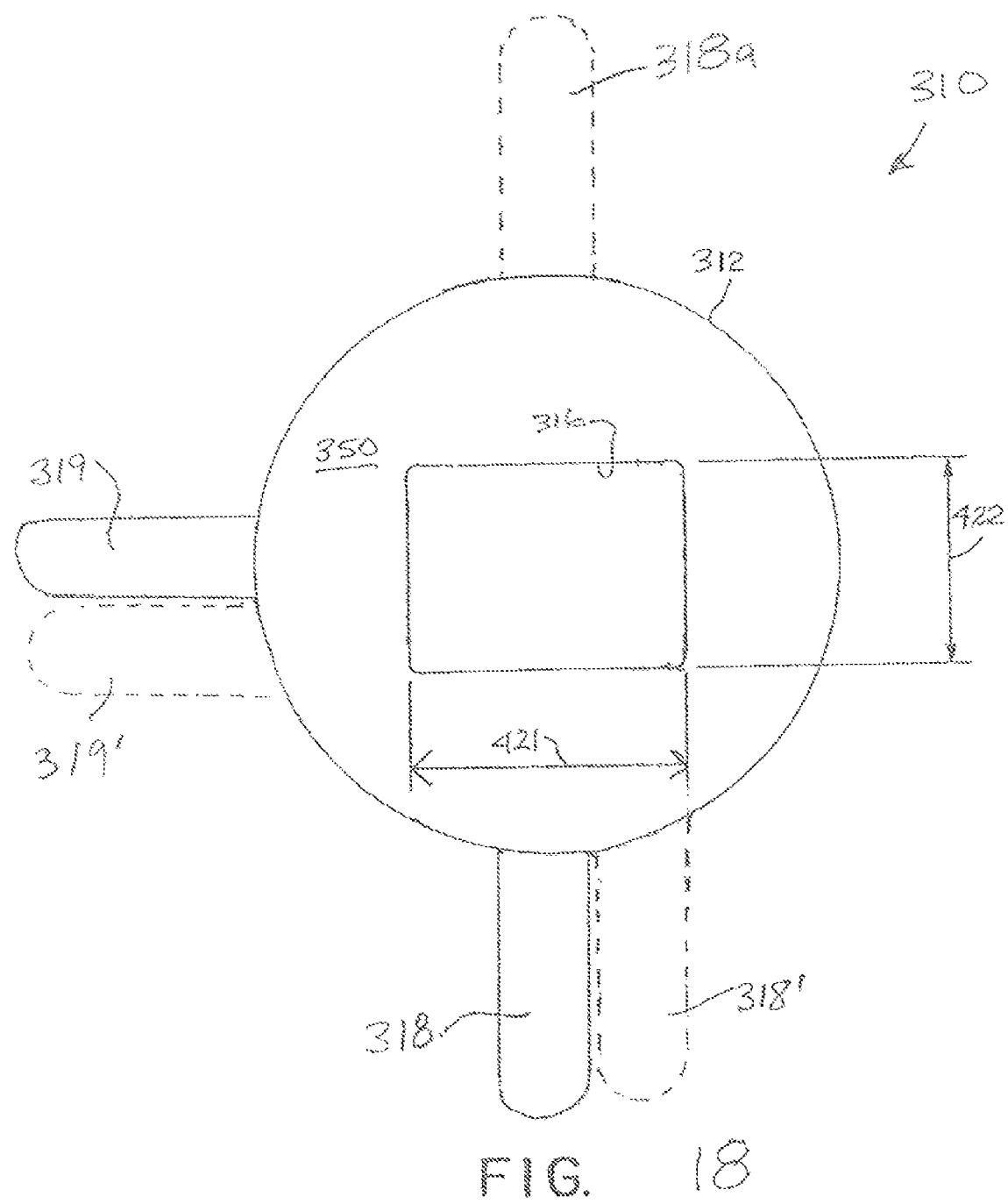
FIG. 18 is a rear elevational view of the shield device shown in FIG. 17.

Referring to FIGS. 14 and 15, another embodiment is shown of the back plate 30. As before, FIG. 14 shows the flat blank for plate 30 and FIG. 15 shows plate 30 after forming. The embodiment shown in FIGS. 14 and 15 is the same as in the embodiment shown in FIGS. 12 and 13 except in the addition of two opposing notches 39. These notches are on opposite sides of the back plate and are on adjacent sides with reference to the clips 32. The notches 39 are a specified dimension 31 from the midpoint of the long side of the back plate 30. The dimension 31 is preferably about 0.15 in. (3.8 mm). The notches 39 accept electronic receptors to the back plate 30 of the receptor holding member 28 with the aid of orthodontic elastics (not shown). The overall length 36, the length 38 between the curled clips 32, and the width 35 of the back plate 30 is the same as in the previous embodiment shown in FIGS. 12-13. FIG. 16 shows receptor 54 held in place on receptor holding member 28 by a pair of orthodontic elastic bands 76 which are received in two spaced pairs of notches 39. Where the receptor 54 is a digital-electronic receptor, data cord 78 extending from the receptor may be secured to and along elongated arm 20 by connector 80, between the collimation plate and the receptor holding member, so that data plug 82 may be positioned outside the patient's mouth.

Other back plate sizes may be used, such as one designed for receptors or film used for children which is smaller than the films used with the back plates shown in FIGS. 12-15. Such a back plate would preferably have a length between the curled clips of about 1.60 in. (4.1 cm) long similar to the embodiments shown in FIGS. 12-15, but, a width of preferably about 1.00 in. (2.5 cm) wide to accommodate size film designed for children.

In operation and use, referring to FIG. 11, the patient's mouth 65 is outlined and the patient's teeth are above and below the elongated arm 20 of the receptor positioning device 10. Teeth 60*a* bite down on and grip biting portion 26 of arm 20. Biting portion 26 may contain elastomeric impression material which conforms to the occlusion pattern of the patient's teeth 60*a*. The receptor holding member 28 is positioned behind the teeth 60*b* to be exposed (on the opposite side of the mouth from teeth 60*a*) and the collimation plate 12 is positioned in adjacent to the patient's mouth 65 and teeth 60*b*. The x-ray machine 62 is positioned to take an x-ray in front of the collimation plate 12 and expose the x-ray film receptor 54. If necessary, the patient or radiographer may use handles 18 to reposition the receptor positioning device for better comfort or aim. Preferably the collimation plate 12 is constructed of a metal and rigidly and fixedly fashioned. The rigid and fixed construction of the receptor positioning device 10 provides the most accurate film exposure because there is minimal opportunity for unwanted movement after positioning the device. The metal collimation plate having a rectangular opening 16 reduces patient exposure by absorbing approximately 50% of primary beam x-radiation for the most commonly prescribed dental radiograph, which is the bitewing. Further, the metal collimation plate reduces aiming error, that is, "cone cuts", which are frequently associated with the rectangular position-indicating device attached to the x-ray machine. Further, the use of the collimation plate of the present invention having a rectangular opening 16 reduces patient exposure to x-radiation by eliminating needless "retakes" of radiographs. The collimation plate 12 of the present invention is compatible with typical round (typically 2.75 in. or 7.0 cm diameter) indicating cylinder device that is typically standard on dental radiographic machines.

Another advantage of a device of the present invention pertains to the absorption of x-rays by the metal receptor holding member 28 which improves the quality of the acquired image on the film 54. The receptor holding member 28 is preferably constructed of a metal. The metal receptor holding member 28 will further reduce patient exposure to x-radiation by absorbing x-radiation that would ordinarily pass through the receptor or film 54. Also, the metal receptor holding member 28 reduces additional secondary or "scatter" radiation that causes degradation of the image.

As shown in FIGS. 1-16, the unitary design of the receptor positioning device 10 eliminates movement of multiple parts which could interfere with the exposure of the film 54. Further, the unitary design sets a fixed x-ray source-to-object distance and an object-to-film distance. Another advantage of the unitary design is the maintenance of uniform magnification and maximization of the sharpness of the acquired image. Another advantage of the receptor positioning device 10 is the preferred all metal design provides a rigid device which is also durable and lends itself to sterilizing using steam, heat or chemical methods. Moreover, the handles 18 which are part of the collimation plate 12 enables the patient to handle the device minimizing patient discomfort and malpositioning.

Another embodiment 310 of the present invention is shown in FIGS. 17-29, which depict a collimation and shielding device substantially as previously described, but removably securable to an otherwise conventional aiming ring of a typical film holding instrument. The aiming ring is used for assisting in positioning the x-ray machine. Referring to FIGS. 17-21, the collimation/shield device 310 includes a substantially flat, circular collimation plate 312 having opposite surface areas 314, 350 which define a substantially central rectangular opening 316 of width 421 and height 422. The preferred collimation plate 312 again includes two elongated handles 318, 319, but at substantially right angles from one another extending outward on two adjacent sides thereof. Alternatively, the collimation/shield may have a pair of handles 318, 318*a* extending outward substantially opposite of one another, as shown in FIGS. 1 and 2 of the previous embodiment. The handles may extend along a radius of the collimation plate 312, as with handles 318, 318*a* and 319, or the handles may be offset or otherwise non-radial, as with handles 318', 319'. The collimation/shield device preferably has at least one handle, but may have more than the two shown in the drawing figures.

To enable facile securing to the ring of a receptor positioning device, the collimation/shield instrument further includes an attachment member 320 having raised corner tabs and a pair of attachment clips for attaching the shield to a typical film holder aiming ring. The attachment member 320 is centrally positioned and may be connected at a flat portion 322 of its front surface or edge to the front or rear surface of the collimator plate, preferably, by welding or other rigid connection, so that the attachment member is fixedly coupled to the collimation shield. Instead of being formed separately, the attachment member 320 may be formed in one piece with the collimation/shield device 310. As described previously, the thickness of the collimation/shield (along with the attachment member) is at least 0.075 in. (1.9 mm) thickness, more preferably 0.080 (2.0 mm) or 0.100 in. (2.5 mm) or more to block excess radiation.

The surface area of the attachment member preferably defines a substantially central rectangular opening 338 of the same dimension as rectangular opening 316 of the collimation/shield device. The opening in the collimation/shield device is oriented similarly and corresponds dimensionally to the film or other receptor to be used in the film holding instrument. In the preferred embodiment shown in FIGS. 17-19, the horizontal dimension 421 is about 1.500 in. (3.8 cm) and the vertical dimension 371 of the opening is about 1.200 in. (3.05 cm) for use with the adult size horizontal and vertical bitewing and periapical examination of patients with normal anatomy and dentitions. Other sizes may be made for small adults, children and other uses. For example, a vertical dimension of about 1.000 in. (2.54 cm) and a horizontal dimension of about 1.500 in. (3.8 cm) is for use for horizontal bitewing and periapical examination of small children (2-8 years) and very small adults or adults with a limited ability to open their mouths, and a vertical dimension of about 1.063 in.

(2.7 cm) and horizontal dimension of about 1.688 in. (4.29 cm) is useful for observing compromised dentitions (with large restorations and height of alveolar crest bone decreased by marginal periodontal disease) that would not be visualized in horizontal bitewing and large adult periapical images.

Figure 23:
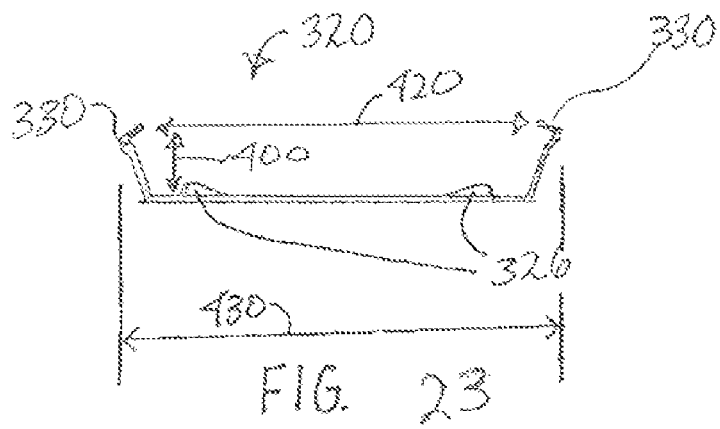
FIG. 23 is a side elevational view of the attachment member shown in FIG. 19.
Figure 24:
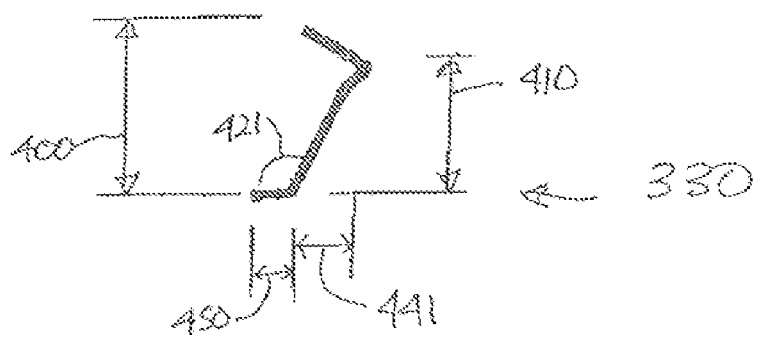
FIG. 24 is a side elevational view of the clip for the attachment member shown in FIG. 19.
Figure 25:
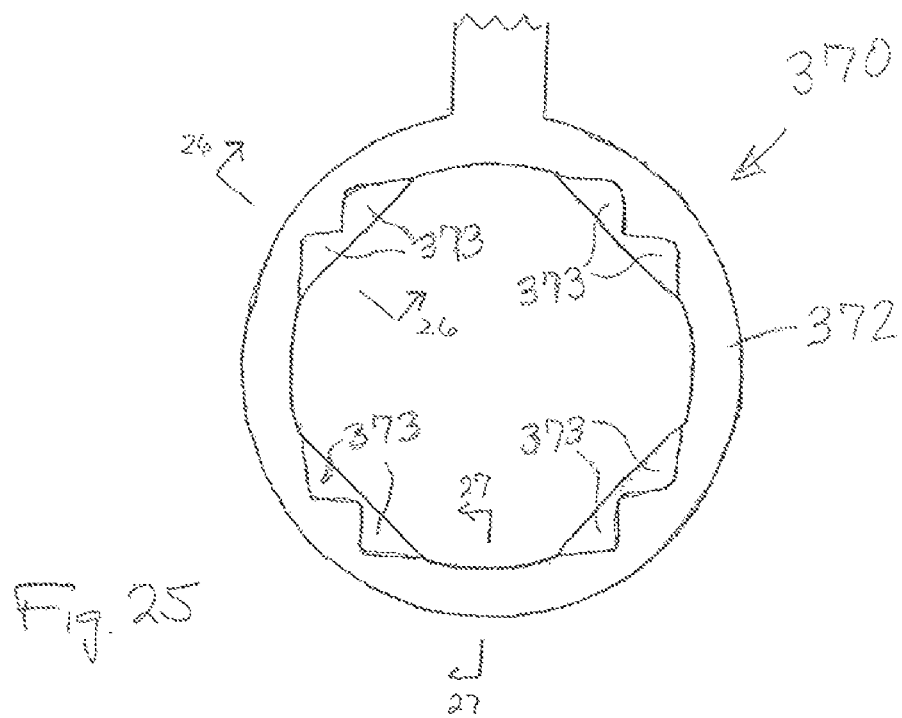
FIG. 25 is a front elevational view of a typical prior art aiming ring with which the present invention is useful.
Figure 28:
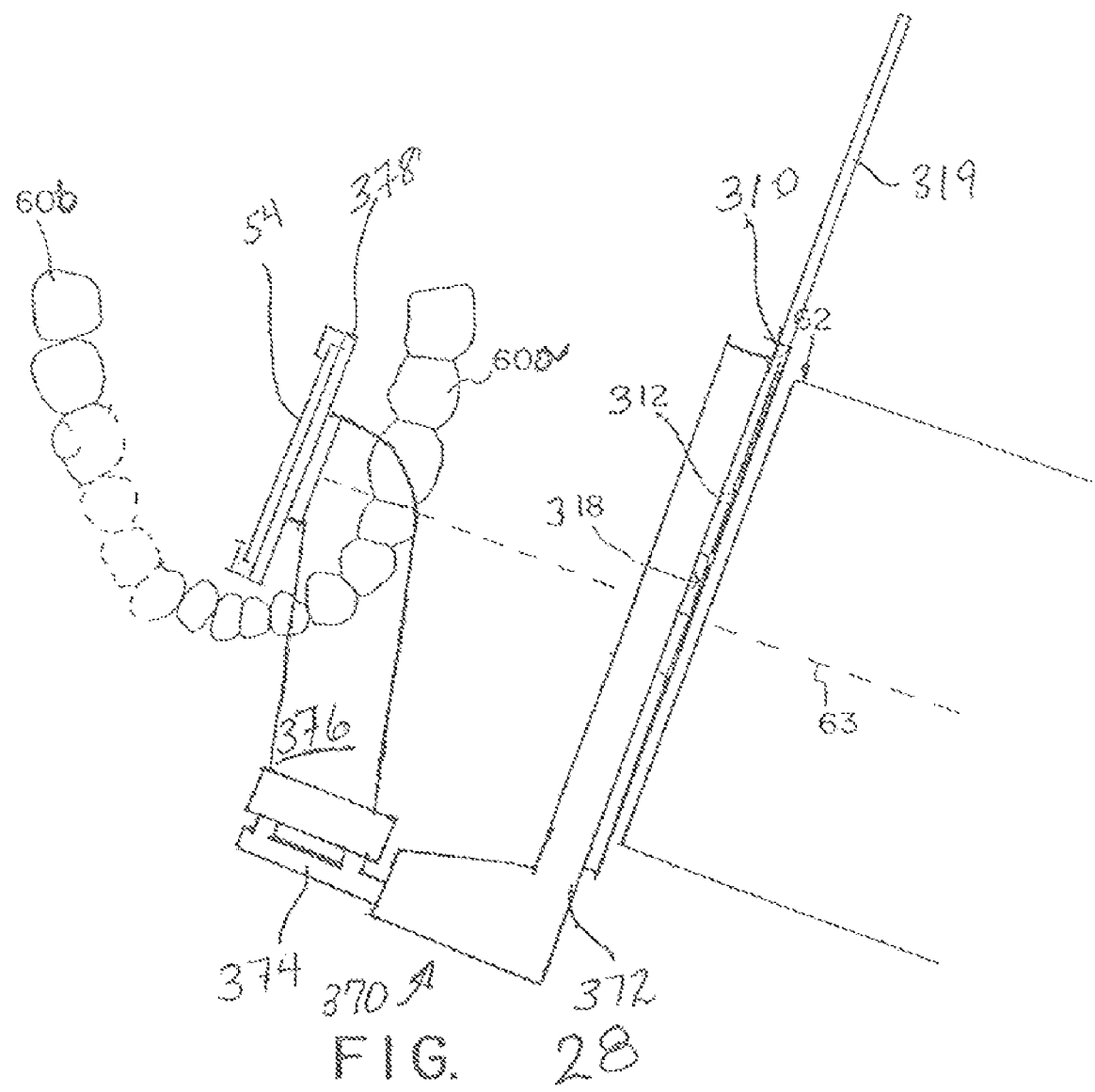
FIG. 28 is a top plan view of the shield device of FIG. 17 attached to a typical intraoral film holding instrument positioned in the patient's mouth, with the x-ray machine in position.
Figure 29:
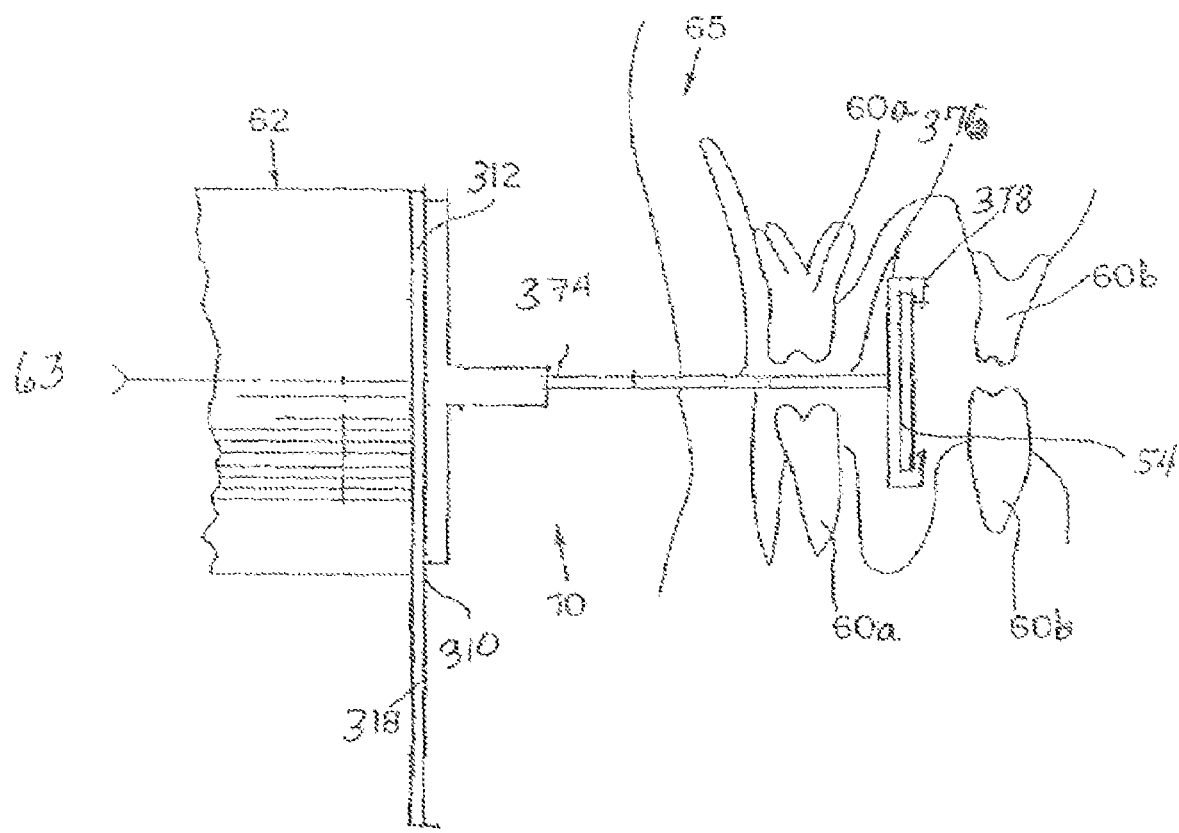
FIG. 29 is a side elevational view of the shield device shown in FIG. 17 attached to a typical intraoral film holding instrument positioned in the patient's mouth, with the x-ray machine in position.

Referring in particular to FIGS. 17, 19-24 and 27, the attachment member 320 has a pair of opposing spring clips 330 designed and adapted to receive and grasp the typical aiming ring 372 on a prior art intraoral film holder 370 (FIGS. 25, 28 and 29). The preferred overall height 400 between the attachment member 320 and the formed clips 330 is about 0.375 in. (9.5 mm). The over all length 340 of the attachment member 20 with the clips bent is preferably about 2.406 in. (6.1 cm) and the length 320 between the bent clips 330 is preferably about 2.125 in. (5.4 cm), as shown in FIGS. 23 and 24. The preferred length of the clip base 450 is about 0.0625 in. (1.6 mm), the preferred angle of bend 421 between the clip base and the clip upright portion is about 112°, the preferred height 410 between the clip base and shoulder is about 0.125 in. (3.2 mm), and the preferred projection 441 of the shoulder is about 0.0625 in. (1.6 mm). Clips 330 engage the inner periphery of aiming ring 372 (FIG. 25) in order to removably secure the attachment member 320 and collimation plate 312 to the ring. This is done by flexing or bending the clips inward, toward each other in direction 415 (FIG. 27), and inserting them into the aiming ring opening. When released, the clips are urged outward by their spring action and secure the collimation/shield device 310 in place over aiming ring 372.

Figure 19:
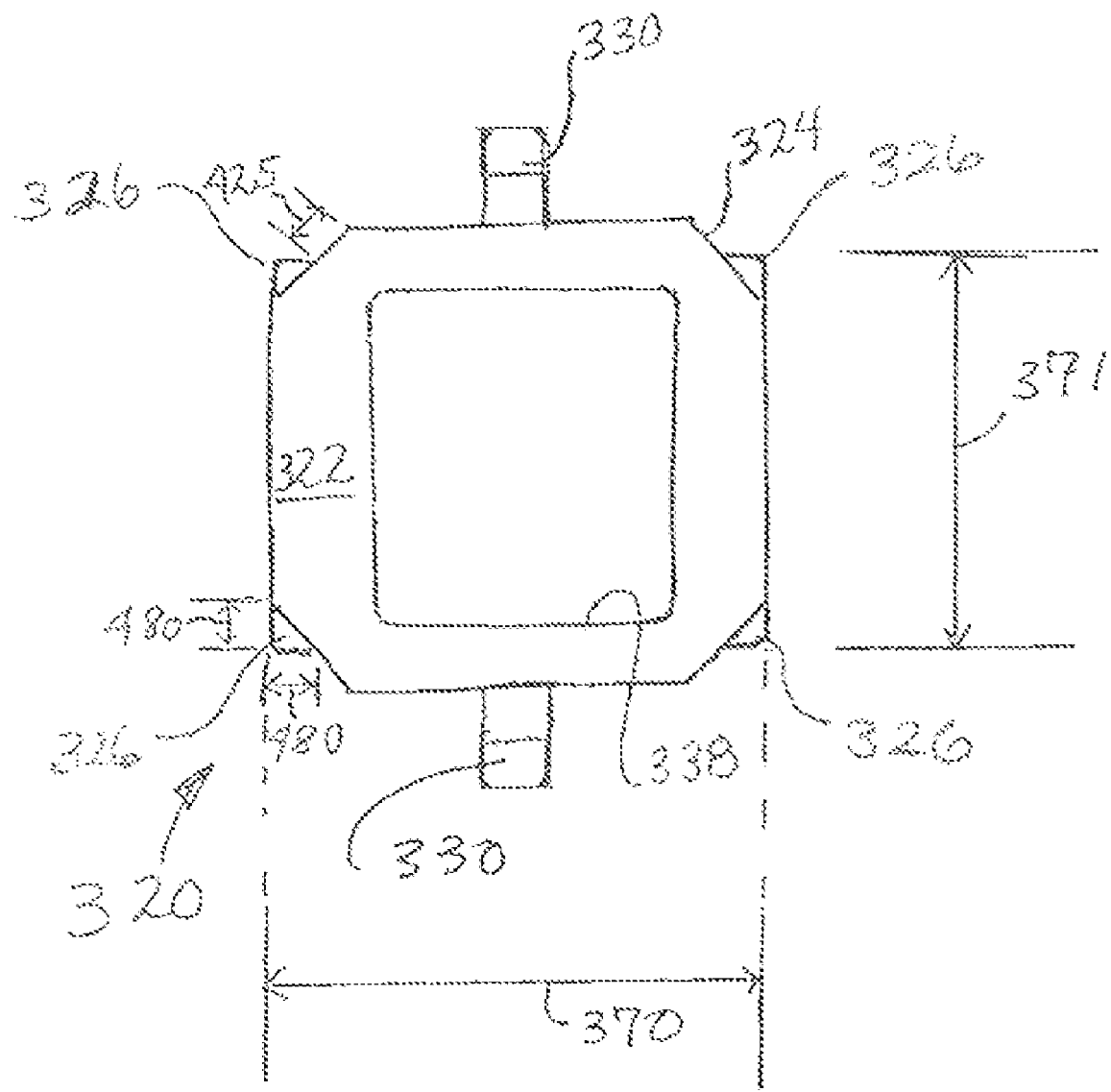
FIG. 19 is a front elevational view of the attachment member shown in FIG. 17.
Figure 20:
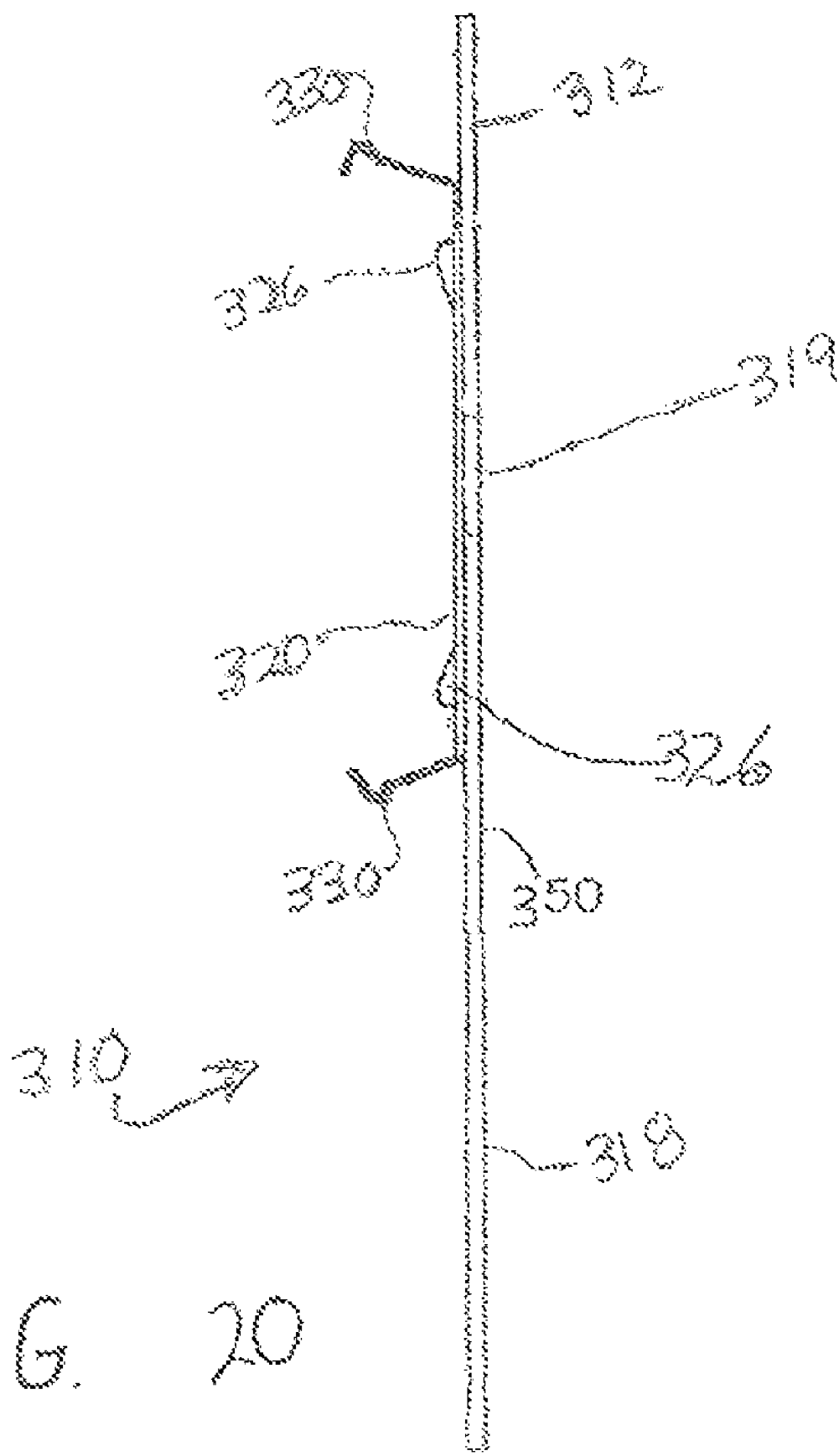
FIG. 20 is a side elevational view of the shield device shown in FIG. 17.
Figure 21:
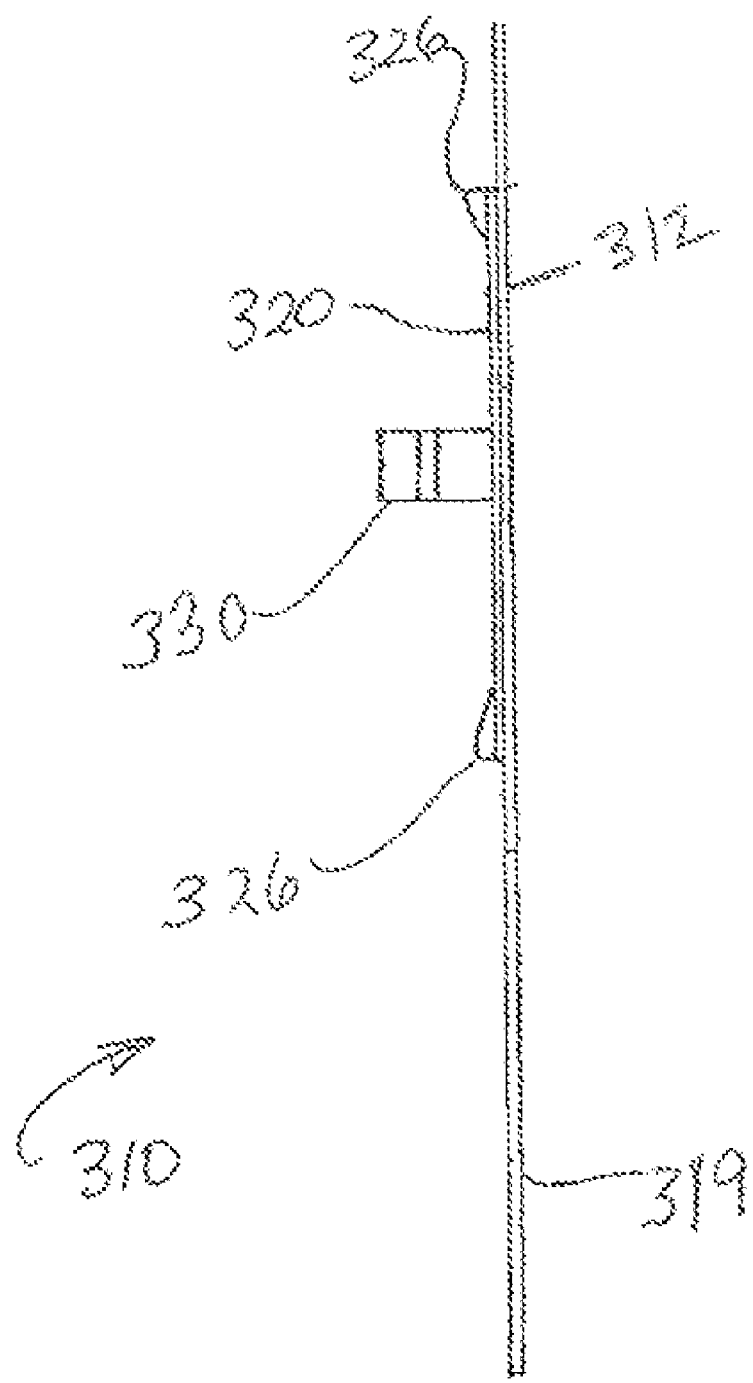
FIG. 21 is a top view of the shield device shown in FIG. 17.
Figure 22:
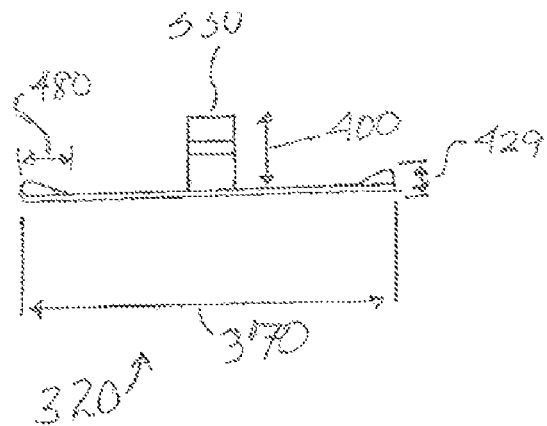
FIG. 22 is a top view of the attachment member shown in FIG. 19.
Figure 26:
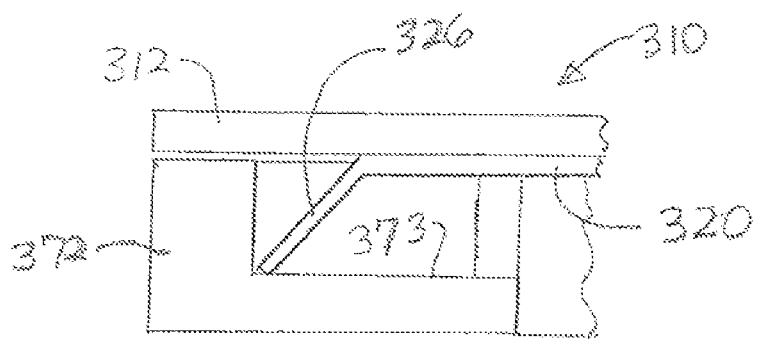
FIG. 26 is a cross-sectional view of the aiming ring of FIG. 25, along line 26-26, showing the insertion of the corner locator tabs of the shield device of FIG. 17 into the index indentations of the aiming ring.
Figure 27:
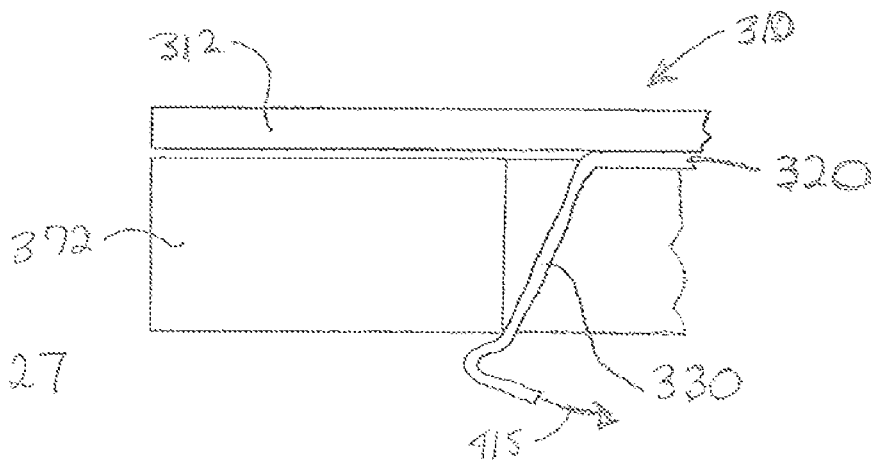
FIG. 27 is a cross-sectional view of the aiming ring of FIG. 25, along line 27-27, showing the clip attachment of the shield device of FIG. 17.

The preferred attachment member 320 also includes four raised corners tabs 326 to align with the index indentations 373 of film holding aiming ring 372 (FIGS. 25 and 26). The pair of recesses in each index indentation 373 permits different orientation of the collimation/shield device. The raised corner tabs are disposed at the corners of the substantially rectangular attachment member 320, and have dimensions 370 and 371, as shown in FIG. 19. The preferred dimension 371 is about 1.1875 in. (3.0 cm) and the preferred dimension 370 is about 1.563 in. (3.9 cm). In this embodiment, the raised corner tabs 326 have a edge width 480 of about 0.185 in. (4.8 mm) and have a rise dimension 429 of about 0.0625 in. (1.6 mm). The corner tabs are each delineated by a notch 324 of a preferred dimension 425 of about 0.25 in. (6.35 mm) and an angle of 45° relative to each side of the attachment member. When collimation/shield device 310 is clipped to the aiming ring, the corner tabs fit into the index indentations 373 of aiming ring 372, as shown in FIG. 26, to locate and prevent rotation of the collimation/shield device relative to the aiming ring. The indentations also permit vertical or horizontal orientation of the substantially rectangular central opening by rotating the shield device 90° prior to attaching to the aiming ring of a typical film holding instrument, thereby providing positive orientation in two positions.

Referring to FIGS. 28 and 29, in operation and use, the collimation/shield device 310 is preferably first clipped to the aiming ring 372. Then the plastic biting portion 376, secured to the film holding instrument 370 by connector 374, is inserted into the patient's mouth 65. The patient's teeth 60a to be x-rayed rest on and bite on the biting portion. The receptor holding member 378 of the biting portion 376 is positioned behind the teeth 60a to be exposed and the aiming ring 372 with the attached shield device 310 is positioned adjacent to the patient's mouth 65 and teeth 60a. The x-ray machine 63 is positioned to take an x-ray in front of the shield device 10 and expose the x-ray film 354. Preferably the collimation/shield device 310 is constructed of metal and rigidly and fixedly fashioned for precise attachment to the typical aiming ring. The patient or radiographer grasps the handles 318, 319 to position and maintain the film holding instrument in the optimal aimed position with better comfort.

As described previously, and as shown in FIGS. 28 and 29, collimation plate 312 is adapted to axially align the x-ray machine's position indicating cylinder device 62 with the receptor 354 shown by the x-ray center line the 63. It does this in two ways. First, the x-ray machine is easily centered because preferably the two devices 312, 62 have substantially the same diameter. Axial offset would be apparent by extension of the outer rim of the x-ray machine position indicating cylinder device 62. Second, substantially full, flat contact of the collimation plate 312 with the x-ray machine's position indicating cylinder device 62, as shown in FIGS. 28 and 29, would assure optimal alignment of the x-ray receptor with the x-ray beam.

The rigid and fixed construction of the shield device 310 provides the most accurate film exposure because there is minimal opportunity for unwanted movement after positioning the device. The metal collimation/shield device having the rectangular opening reduces patient exposure by absorbing approximately 50% of the primary beam x-radiation for most commonly prescribed dental intraoral radiographs, which are the bitewing and periapical views. As with the previous embodiments, the metal collimation/shield device of FIGS. 17-29 reduces aiming error, or cone cuts, and eliminates needless retakes of radiographs for typical prior art film holding instruments.

The collimation/shield device 310 of the present invention is compatible with a round indicating cylinder device 62 of 2.75 in. (7.0 cm) diameter that is typically standard on dental radiographic machines and with the round aiming ring 372 of 2.75 in. (7.0 cm) diameter that is a component of a typical intraoral film holder 70. The unitary design of the shield device 10 permits precise attachment to the typical aiming ring 372, thus, preventing additional movement that could interfere with the exposure of the film 54. Another advantage of the collimation/shield device is that, prior to attaching, the orientation of the central opening 316 of the shield can be rotated 90° relative to the aiming ring and selected film holding member of typical receptor positioning instruments, thus, permitting vertical or horizontal orientation. Another advantage of the collimation/shield device 310 is the preferred all metal design provides a rigid device which is also durable and lends itself to sterilization using steam, heat or chemical methods. Moreover, the handles 318, 319 which are part of the collimation/shield device 310 enable the patient to handle the device minimizing patient discomfort and malpositioning.

Another preferred embodiment of the invention is depicted in FIGS. 30-33 for use with a receptor holding member having connector arm or rod that would otherwise use a conventional aiming ring. Collimation and shielding device 410 includes a substantially flat, circular collimation shield 412 preferably made of a metal such as 302 stainless steel of thickness of from about 0.051 in. (1.3 mm) to about 0.100 in (2.5 mm) or more, preferably at least about 0.072 in. (1.8 mm), to block and attenuate unwanted radiation from entering the patient's mouth. (Features of this embodiment that correspond with those of previous embodiments are designated with a leading 4, e.g., shield 410 instead of shield 310.) Optionally, the collimation shield 412 is made of a high gravity compound, such as an injection-moldable nylon, polypropylene or other plastic matrix filled with tungsten or other metal powder, which has sufficient radiation attenuation properties and is preferably has a thickness of at least about 0.500 in. (12.7 mm).

Figure 30:
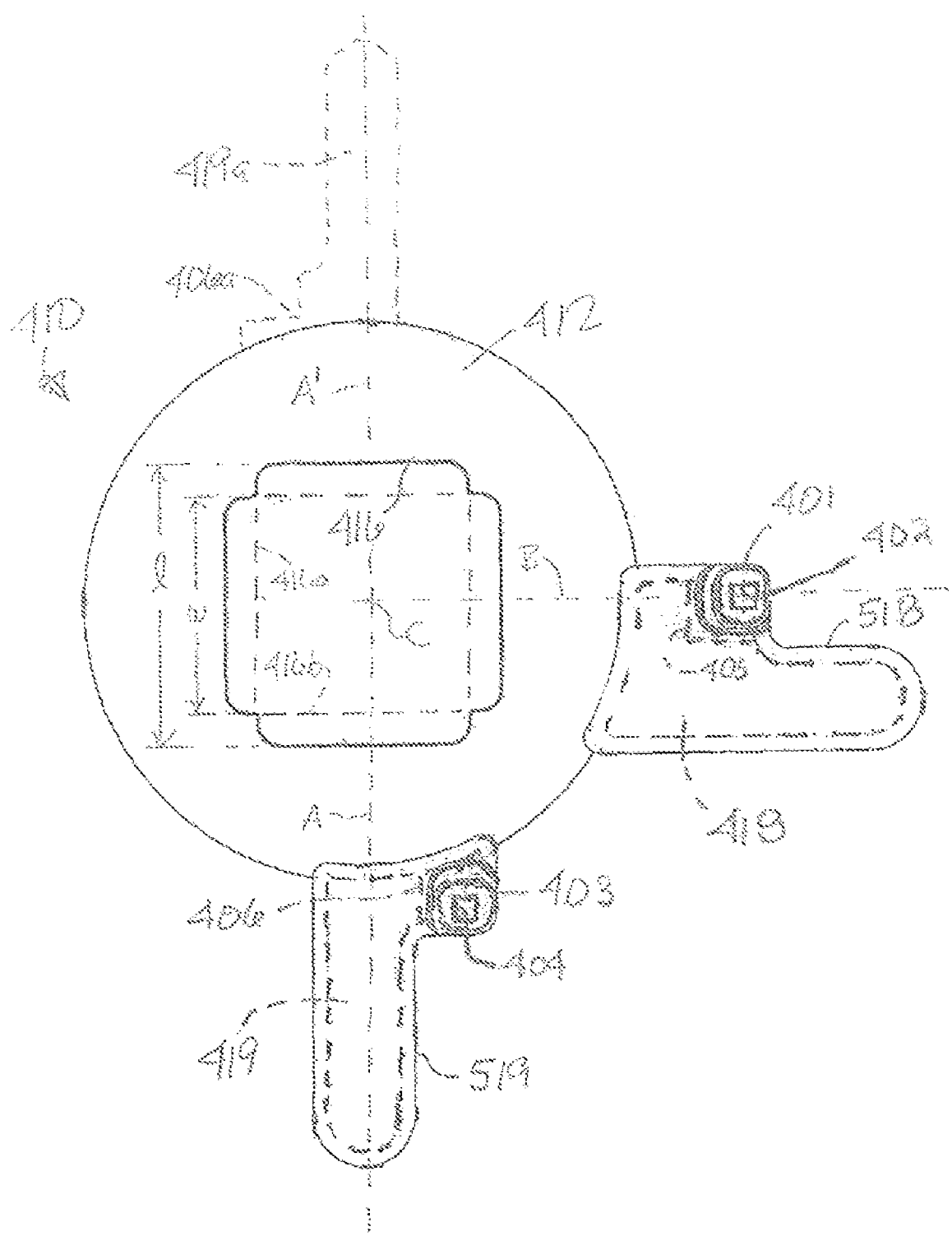
FIG. 30 is a front elevational view of another preferred receptor positioning device shield, handle grips and arm openings of the present invention.

A pair of elongated handles 418, 419 extend outward on two adjacent sides of shield 412 at substantially right angles from one another. Preferably, the handles 418, 419 are made of the same material as, and integral with, collimation shield 412, for example by stamping out of a single piece of the stainless steel, so as to have the same thickness as the shield 412. Alternatively, the collimation shield may have a pair of handles 419, 419a extending outward substantially opposite of one another, as shown in FIG. 30. The handles may extend along a radius extending from the center of the collimation plate 412, as shown by mirror image handles 419 and 419a having their longitudinal axes aligned along radii A and A', respectively, extending from the center C of the shield opening 416. Alternatively, the handles may be offset from the radius or otherwise non-radial, as with handle 418, shown with its longitudinal axis parallel to and offset from radius B. The collimation/shield device preferably has at least one handle, but may have more than the two shown in the FIGS. 30-33. More preferably, the device has at least one radial handle and one non-radial handle.

Figure 31:
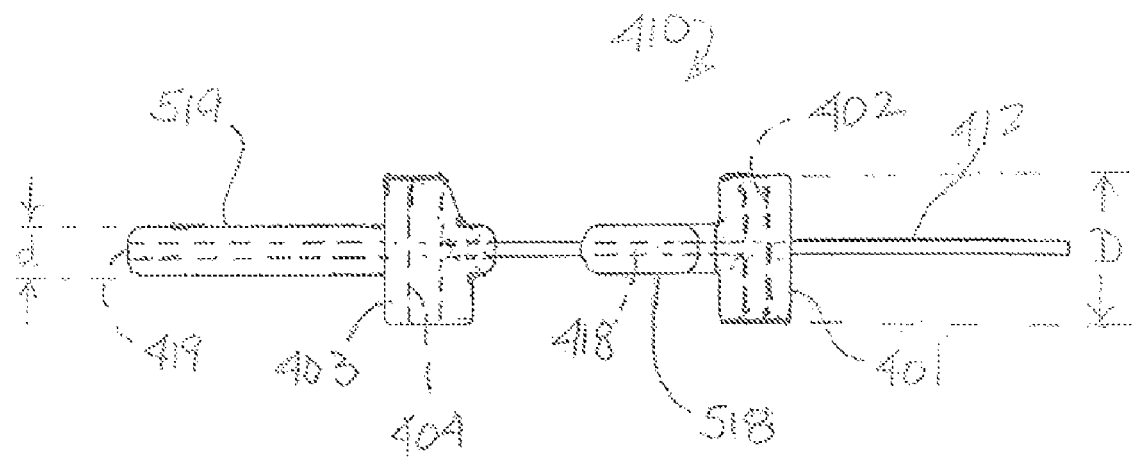
FIG. 31 is a side elevational view of the receptor positioning device of FIG. 30.
Figure 32:
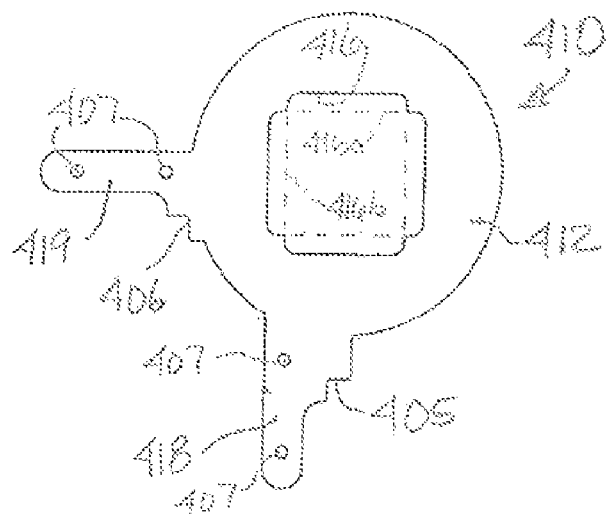
FIG. 32 is a rear elevational view, rotated 90°, of the shield portion of the positioning device of FIG. 30.

To facilitate handling and positioning of the collimation and shield device 410, and to enable connection with a connector arm or rod for a film or receptor holding member, handles 418 and 419 have secured thereover polymeric handle grips 518, 519. Grips 518, 519 may be molded or cast over shield handles 418, 419, respectively, but may also be separately made and adhered or otherwise secured to the shield handles. Preferably, the grips are made of injection molded nylon or polypropylene. Openings 407 in the stainless steel handles 418 and 419 permit the molded grip material to connect on opposite sides for better strength. As shown in FIG. 31, grips 418, 419 have a thickness "d" substantially greater than that of shield 412. Handles 418 and 419 not only permit positioning by the dental x-ray operator, but, more importantly, permit the patient to hold onto the handle during the x-ray exposure for greater patient comfort. Unlike prior art x-ray positioning devices, where the patient must secure the device in this mouth during x-ray exposure solely by gripping the biting surface, which may lead to patient discomfort and motion artifacts on the exposed x-ray film or electronic receptor, the present invention permits the patient to hold the receptor positioning device with his own hand throughout the x-ray procedure and gain a greater sense of comfort. The patient does not have to rely solely on gripping the biting surface tightly, but may rely also on his own hand holding the device. This will also permit the operator to more accurately position the receptor in the patient's mouth to expose the desired teeth. The dental x-ray operator then proceeds to align the x-ray machine with the substantially flat surface of the collimation plate 412 and pass x-rays through the opening 416 in the collimation plate to expose a film or electronic receptor on the receptor holder in the manner described in connection with previous embodiments. Preferably, the patient grasps one of the handles most convenient to his hand during both the positioning of the receptor within his mouth, and also during the operation and exposure by the x-ray machine.

Near the bases of handles 418 and 419 are cut-out sections 405 and 406, respectively, which provide reinforcement for passage of rectangular arm holder openings 402 and 404 in grips 418 and 419, respectively (FIG. 31). Preferably, the cut-outs are adjacent at least two sides of the rectangular openings 402, 404. These opening 402, 404 are for passage of a connecting arm or rod to the receptor holding member, which will be discussed further below. Openings 402 and 404 pass through reinforced grip sections 401 and 403, respectively. These reinforced sections 401 and 403 have thickness D substantially greater than thickness d of the remainder of grips 518 and 519 (FIG. 31). The rectangular openings may be aligned with a radius of the shield, such as is shown in FIG. 30 by opening 402 wherein a radius B that is parallel to the upper and lower sides of the opening also passes through the opening. The rectangular openings may also be non-radially aligned (or radially offset), as shown by opening 404, where a radius, A which is parallel to right and left sides of the opening, does not pass through the opening. The device may have only one, or more than two of the connector arm or rod openings, and preferably has at least one radially aligned and one non-radially aligned opening. A radially aligned arm holder opening 402 is preferred for posterior teeth film positioning arms, where the x-ray receptor holding member is to be offset from the shield opening 416, and a non-radially aligned arm holder opening 404 is preferred for anterior teeth film positioning arms, where the x-ray receptor holding member is to be centered with the shield opening 416.

Figure 33:
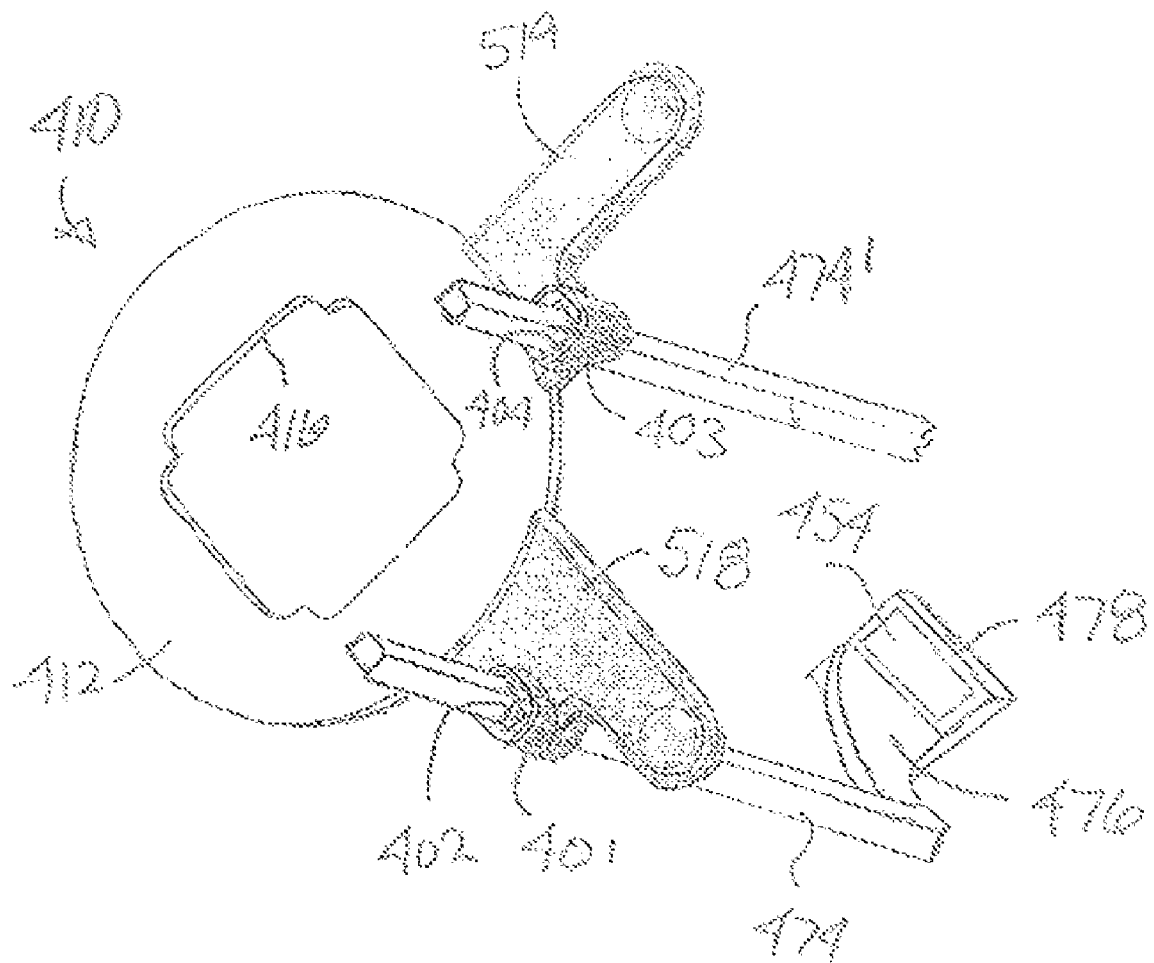
FIG. 33 is a perspective view of the receptor positioning device of FIG. 30 with the receptor holding member and securing arm.

As shown in FIG. 33, grip openings 402, 404 permit passage of and connection to connector arm or rod in position 474 or alternatively, position 474'. Openings 402, 404 are preferably sized to provide a tight fit to permit insertion and sliding adjustment of connector arm 474. More preferably, openings 402, 404 each have a molded in tab that is sized to interfere with, but permit sliding of, arm 474, so that it may be adjusted to the proper linear position and remain in place during the x-ray procedure. Connector arm 474 is secured at one end to film or digital receptor holding member 478, also known as a basket, by plastic biting portion or bite block 476, which is to be inserted into the patient's mouth, and held by the patient's teeth during the x-ray exposure. The positioning of the receptor holding member and bite block in the patient's mouth is the same as that shown in the previous embodiment of FIGS. 17-29 for those that normally use conventional aiming rings. (Alternatively, a receptor holding member, bite block and securing arm of the embodiments of FIGS. 1-16 may be employed with the collimation and shielding device 410 of FIGS. 30-32.) A removable film or digital-electronic receptor 454 is secured to receptor holding member 478. Biting portion 476 may contain elastomeric impression material on opposite biting surfaces that may be used to create teeth impressions and register with the unique occlusion pattern of the patient's teeth, as shown in FIGS. 3-8. Arm 474 is preferably non-circular in cross-section, and preferably rectangular as shown, so that collimation shield device 410 does not rotate with respect to the receptor holding member 478.

A central opening 416 permits passage of x-rays from the x-ray machine's position indicating cylinder device 62 when it is axially aligned with the collimation and shielding device 410. Preferably, the center of opening 416 is coincident with the center of shield 412. Central opening 416 as shown is the outermost outline of two intersecting non-square rectangles 416a (shown in portrait orientation) and 416b (shown in landscape orientation) each having side ratios approximately that of the film or detector for the teeth x-ray image. The resulting opening is cross-shaped, where the length l of the cross-members is equal to the longer side length of the rectangles 416a, 416b, and the width w of the cross-members is equal to the shorter side length of the rectangles 416a, 416b. The cross-shaped opening 416 permits either vertical (portrait) or horizontal (landscape) orientation of a film or electronic receptor. This cross-shaped opening also permits the orientation of device 410 to be rotated by 90° if it is desired to change orientation of the handles with respect to the patient's mouth or the x-ray machine, or to change the position of the receptor holding member 478 with respect to the opening 416 in the shield 412. The different radial and non-radial orientation of connector arm openings 402, 404 also permits variation of the position of the receptor holding member with respect to openings 416a and 416b for best x-ray view of the desired patient's teeth. Additionally, the openings 416a and 416b may be sized in different l×w increments, such as for standard sizes 0, 1 or 2, or any other size required for a child or adult patient. In each instance, the size and orientation of the receptor holding member is preferably made to match the opening size and orientation of opening 416a or 416b to minimize passage of extraneous and unwanted x-radiation into the patient's mouth. Although the cross-shaped opening permits somewhat more extraneous radiation to enter the patient's mouth compared to the rectangular opening sized and oriented to the specific x-ray receptor size and orientation as described in previous embodiments, the shield of the present invention is still expected to reduce x-ray exposure by about 30-45% compared to prior art aiming rings. The shield absorption of this excess radiation also reduces degradation of the image on the x-ray receptor due to secondary scatter of excess radiation in the patient's mouth.

The present invention, and particularly the embodiment of FIGS. 30-33, thus provides for improved patient comfort by permitting patient participation in and holding of a collimation plate handle during device positioning and x-ray exposure. The different radial and non-radial alignment of multiple handles and arm holders, along with the collimation plate opening that accommodates both vertical and horizontal receptor positioning, permits maximum flexibility and use of the receptor position device for different size patients and different tooth exposures. These advantages are accomplished while still reducing unwanted x-ray exposure to the patient's mouth and enabling better x-ray image quality.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. A receptor positioning device for taking dental bitewing radiographs of a patient's teeth comprising:
   a receptor holding member adapted to receive a receptor for exposing x-radiation from the x-ray machine;
   an arm secured to the receptor holding member and including a biting surface for engaging the patient's teeth to secure the device in the patient's mouth; and
   a collimation plate having a substantially flat surface for aligning with an x-ray machine and made of a material and sized sufficient to attenuate undesired radiation from the patient's mouth, an opening in the plate surface for passage of radiation from the x-ray machine and at least partially corresponding in shape to a receptor in the receptor holding member, and a handle extending away from the plate for positioning the device, the collimation plate including a reinforced arm holder adjacent a base of the handle and having an opening therein for slidably receiving the arm and removably securing the collimation plate to the receptor holding member.

2. The device of claim 1 wherein the collimation plate is made of a metal and further including a polymeric grip on the handle incorporating the arm holder, the collimation plate having a cut-out portion adjacent a base of the handle through which the arm-receiving opening of the polymeric arm holder extends.

3. The device of claim 1 wherein the arm-receiving opening of the arm holder is rectangular and the collimation plate has a cut-out portion adjacent a base of the handle on at least two sides of the rectangular arm-receiving opening.

4. The device of claim 1 including a pair of handles, each handle having an arm holder with an arm-receiving rectangular opening, wherein one of the arm-receiving rectangular openings is radially aligned with the collimation plate opening and the other of the arm-receiving rectangular openings is non-radially aligned with the collimation plate opening.

5. The device of claim 1 including a pair of handles, each handle having a polymeric portion with an arm-receiving rectangular opening, wherein one of the handles is radially aligned with the collimation plate opening and the other of the handles is non-radially aligned with the collimation plate opening.

6. The device of claim 1 wherein the collimation plate is made of a high gravity compound, the collimation plate having a cut-out portion adjacent a base of the handle through which the arm-receiving opening of the arm holder extends.

7. The device of claim 1 wherein the opening is a cross-shaped intersection of two non-square rectangles having members with a length and a width, the length of the cross members being equal to a longer side length of the rectangles and the width of the cross members being equal to a shorter side length of the rectangles.

8. The device of claim 1 wherein the opening is a cross-shaped intersection of two non-square rectangles having members with a length and a width, the length of the cross members being equal to a longer side length of the rectangles and the width of the cross-members being equal to a shorter side length of the rectangles.

9. A receptor positioning device for taking dental bitewing radiographs of a patient's teeth comprising:
   a receptor holding member adapted to receive a receptor for exposing x-radiation from the x-ray machine;
   an arm secured to the receptor holding member and including a biting surface for engaging the patient's teeth to secure the device in the patient's mouth; and
   a collimation plate having a substantially flat surface for aligning with an x-ray machine and made of a material and sized sufficient to attenuate undesired radiation from the patient's mouth, an opening in the plate surface for passage of radiation from the x-ray machine, the opening being cross-shaped and corresponding in shape to an outline of two intersecting non-square rectangles to permit passage of x-rays to a receptor in the either a vertical or horizontal position in the receptor holding member, and a handle extending away from the plate for positioning the device, the collimation plate being securable to the arm securing the receptor holding member.

10. The device of claim 9 wherein the collimation plate is made of a metal and further including a polymeric grip on the handle incorporating an arm holder adjacent a base of the handle and having an opening therein for slidably receiving the arm and removably securing the collimation plate to the receptor holding member.

11. The device of claim 10 wherein the arm-receiving opening of the arm holder is rectangular and the collimation plate has a cut-out portion adjacent a base of the handle on at least two sides of the rectangular arm-receiving opening.

12. The device of claim 10 including a pair of handles, each handle having an arm holder with an arm-receiving rectangular opening, wherein one of the arm-receiving rectangular openings is radially aligned with the collimation plate opening and the other of the arm-receiving rectangular openings is non-radially aligned with the collimation plate opening.

13. The device of claim 9 including a pair of handles, each handle having a polymeric portion with an arm-receiving rectangular opening, wherein one of the handles is radially aligned with the collimation plate opening and the other of the handles is non-radially aligned with the collimation plate opening.

14. The device of claim 9 wherein the collimation plate is made of a high gravity compound.

15. A receptor positioning device for taking dental bitewing radiographs of a patient's teeth comprising:
   a receptor holding member adapted to receive a receptor for exposing x-radiation from the x-ray machine;
   an arm secured to the receptor holding member and including a biting surface for engaging the patient's teeth to secure the device in the patient's mouth; and
   a collimation plate having a substantially flat surface for aligning with an x-ray machine and made of a material and sized sufficient to attenuate undesired radiation from the patient's mouth, an opening in the plate surface for passage of radiation from the x-ray machine, and a pair of handles extending away from the plate for positioning the device, one of the handles being radially aligned with the collimation plate opening and the other of the handles being non-radially aligned with the collimation plate opening, the collimation plate being securable to the arm securing the receptor holding member.

16. The device of claim 15 wherein the collimation plate is made of a metal and further including polymeric grips on the handles incorporating an arm holder adjacent a base of the handle and having an opening therein for slidably receiving the arm and removably securing the collimation plate to the receptor holding member.

17. The device of claim 16 wherein the arm-receiving opening of the arm holder is rectangular and the collimation plate has a cut-out portion adjacent a base of the handle on at least two sides of the rectangular arm-receiving opening.

18. The device of claim 16 including one arm-receiving rectangular opening radially aligned with the collimation plate opening and another arm-receiving rectangular opening non-radially aligned with the collimation plate opening.

19. The device of claim 15 wherein the collimation plate is made of a high gravity compound.

20. A method for taking dental bitewing radiographs of a patient's teeth comprising:
   providing a receptor positioning device including a receptor holding member adapted to receive a receptor for exposing x-radiation from the x-ray machine, an arm secured to the receptor holding member and including a biting surface for engaging the patient's teeth to secure the device in the patient's mouth, and a collimation plate having a substantially flat surface for aligning with an x-ray machine and made of a material and sized sufficient to attenuate undesired radiation from the patient's mouth, an opening in the plate surface for passage of radiation from the x-ray machine, and a pair of handles extending away from the plate for positioning the device, one of the handles being radially aligned with the collimation plate opening and the other of the handles being non-radially aligned with the collimation plate opening, the collimation plate being secured to the arm securing the receptor holding member;
   providing a receptor on the receptor holding member;
   positioning the receptor holding member in the patient's mouth and the patient's teeth on the biting surface;
   adjusting the position of the receptor positioning device by the patient grasping a handle extending away from the collimation plate;
   aligning an x-ray machine with the substantially flat surface of the collimation plate; and
   passing radiation from the x-ray machine through the opening of the collimation plate to expose the receptor, while the patient's hand grasps the collimation plate handle.

\* \* \* \* \*